US006252130B1

(12) United States Patent
Federoff

(10) Patent No.: US 6,252,130 B1
(45) Date of Patent: Jun. 26, 2001

(54) PRODUCTION OF SOMATIC MOSAICISM IN MAMMALS USING A RECOMBINATORIAL SUBSTRATE

(75) Inventor: Howard Federoff, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 08/747,328

(22) Filed: Nov. 12, 1996

Related U.S. Application Data

(60) Provisional application No. 60/006,622, filed on Nov. 13, 1995.

(51) Int. Cl.[7] .......................... C12N 15/09; C12N 15/00; C12N 15/63; C12N 5/00
(52) U.S. Cl. .............................. 800/14; 800/18; 800/21; 800/24; 514/44; 424/93.2; 435/462
(58) Field of Search .............................. 800/2, DIG. 1–4, 800/18, 21, 24, 13; 438/172.3; 514/44; 424/93.2; 435/172.3, 462

(56) References Cited

U.S. PATENT DOCUMENTS

| 4,959,317 | 9/1990 | Sauer ................................ 435/172.3 |
| 5,527,695 | 6/1996 | Hodges et al. .................... 435/172.3 |
| 5,962,315 | * 10/1999 | Beach et al. .......................... 435/325 |

OTHER PUBLICATIONS

K. Araki et al., Proc. Natl. Acad. Sci. USA, " Site–specific recombination of a transgene in fertilized eggs by transient expression of Cre recombinase, " Jan. 1995, vol. 92, pp. 160–164.*
W. Baubonis et al., Nucleic Acids Research, "Genomic targeting with purified Cre recombinase," 1993, vol. 21, No. 9, pp. 2025–2029.*
Wall, R. J. Transgenic Livestock: Progress and Prospects for the Future, Theriogenology, vol. 45, pp. 57–68, 1996.*
Orkin et al. Report and Recommendations of the Panel to Assess the NIH Investment in Research on Gene Therapy. Distributed by the National Institutes of Health, Bethesda, MD, Dec. 7, 1995.*
Krimpenfort et al. Generation of Transgenic Dairy Cattle Using 'In Vitro'Embryo Production. Bio/Technology, vol. 9, pp. 844–847, Sep. 1991.*
O'Gorman et al. Recombinase–Mediated Gene Activation and Site–Specific Integration in Mammalian Cells. Science, vol. 251, pp. 1351–1355, Mar. 15, 1991.*
Bradley et al. Modifying the Mouse: Design and Desire. Bio/Technology, vol. 10, pp. 534–539, May 1992.*
Hogan et al. Manipulating the Mouse Embryo. Cold Spring Harbor Publishing. pp. 88 and 188, 1986.*
Sambrook et al. Molecular Cloning A Laboratory Manual. Cold Spring Harbor Laboratory Press. pp. 9.31–9.57 and 18.60–18.61, 1989*
Dale et al., "Gene Transfer With Subsequent Removal of the Selection Gene from the Host Genome, " Proc. Natl. Acad. Sci. U.S.A., 88:10558–10562 (1991).
Jayram, "Mechanism of Site–Specific Recombination: The Flp Paradigm, " Nucleic Acids and Molecular Biology, 8:268–286 (1994).
Smith et al. "A Site–Directed Chromosomal Translocation Induced in Embryonic Stem Cells by Cre–lox P Recombination," Nature Genetics, 9:376–385 (1995).
Lasko et al., "Targeted Oncogene Activation by Site–Specific Recombination in Transgenic Mice, " Proc. Nat'l Acad. Sci. USA, 89:6232–36 (1992).
Orban et al., "Tissue–and Site–Specific DNA Recombination in Transgenic Mice, " Proc. Nat'l Acad. Sci. USA, 89:6861–65 (1992).

* cited by examiner

Primary Examiner—Jill D. Martin
(74) Attorney, Agent, or Firm—Nixon Peabody LLP

(57) ABSTRACT

The present invention relates to recombinatorial substrates which include a promoter, a terminator, a gene positioned 3' to the terminator and whose expression is to be controlled, and recombination sites on each side of the terminator such that when the substrate is treated with a specific recombinase the gene will be expressed. Recombinatorial substrates which have a promoter, a gene to be controlled, and recombination sites on each side of the gene which when treated with recombinase delete the gene are also provided. Also enclosed are methods of creating transgenic mammals carrying the recombinatorial substrate and methods for activating the recombinatorial substrate.

18 Claims, 12 Drawing Sheets

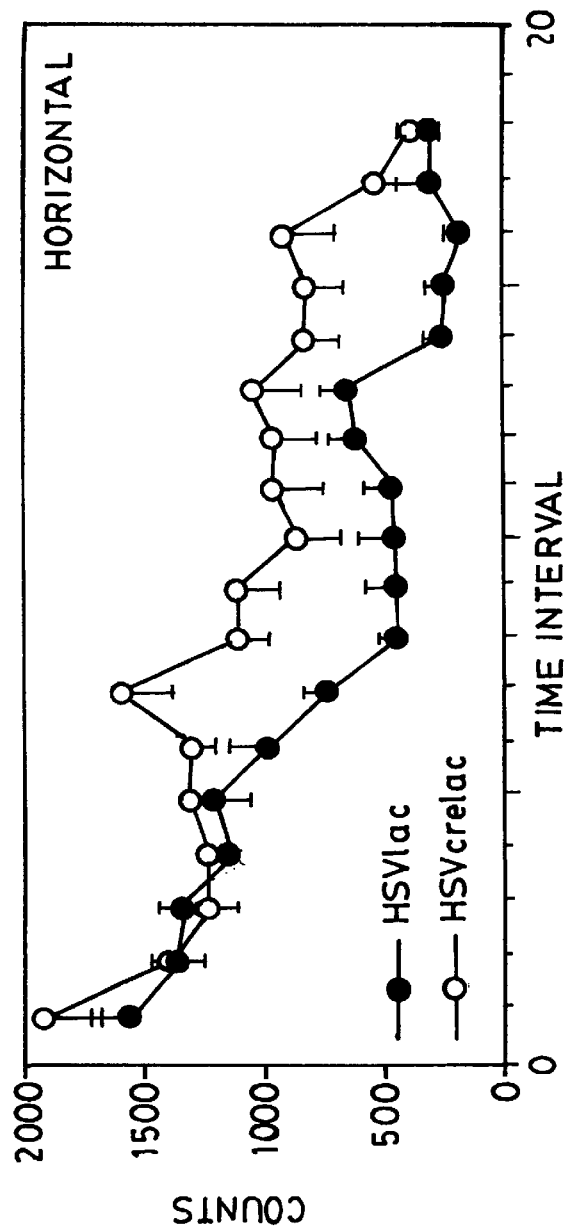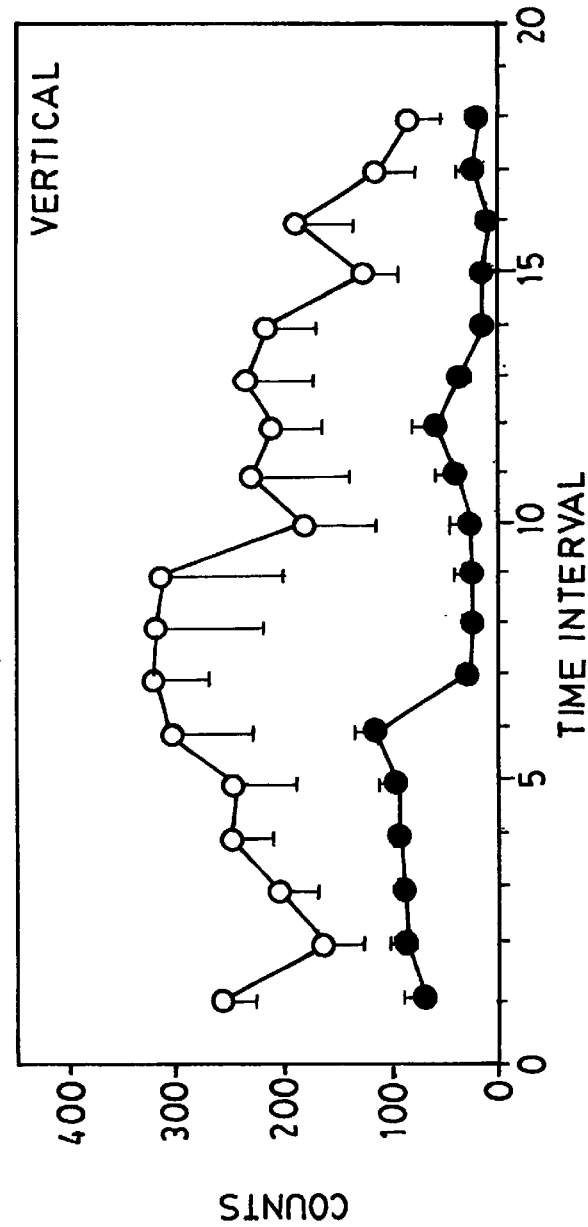

PRODUCTION OF SOMATIC MOSAICISM IN MAMMALS USING A RECOMBINATORIAL SUBSTRATE

This application claims the benefit of U.S. Provisional Patent Application Ser. No. 60/006,622, filed Nov. 13, 1995.

The subject matter of this application was made with support from the United States Government under Grant No. HD 31300 from the Public Health Service and Grant No. IBN-9522307 from the National Science Foundation. The United States Government may retain certain rights.

FIELD OF THE INVENTION

The present invention relates to DNA molecules encoding recombinatorial substrates which can be activated to effect a gain or loss of function of genes in somatic and/or germ cells of a mammal, methods for creating the recombinatorial substrates, and methods for activating the recombinatorial substrates in mammals.

BACKGROUND OF THE INVENTION

Creating focal genetic modifications in an intact animal is a powerful approach for studying the cellular interactions that underlie the development and function of tissues and organs. This method has been used to great advantage in Drosophila, facilitating the study of developmental questions relating to the autonomy of gene actions, restriction of cell fate and growth pattern of specific tissues. The approach involves the generation of genetic mosaics, tissues in which some cells differ from their neighbors by a single mutation, effecting either a gain or loss of function phenotype. Through the analysis of mutant and wild-type cells within mosaics patches, it is possible to draw inferences about interacting cells and in some cases the molecules and pathways subserving cellular communication.

The application of mosaic analysis to the study of nervous system function has the potential to yield a wealth of information because it should allow for an assessment of the function of particular gene products within individual cells that are part of a network. Thus, in tissues such as the nervous system where functional information resides not only in the nature and number of its constituent cells, but also in the manner in which they connect and temporally interact, it is essential that strategies be employed that neither unintentionally change the network nor eliminate some of the cellular constituents. Overall, the ideal strategy should permit stable genetic modification with precise temporal and spatial control.

Implicit in the use of genetic mosaic analysis is the ability to distinguish mutant from normal cells by the use of markers. The preferred marker is one which is gratuitous thus causing no cell damage, cell-autonomous so that cellular level resolution of mosaicism can be reliably scored, and having a short half-life to improve temporal analysis of the tissue after genetic modification.

Genetic mosaics have been generated in Drosophila by induction of mitotic recombination (reviewed in Ashburner, M., *Drosophila: A Laboratory Handbook*, Cold Spring Harbor Laboratory Press, Cold Spring Harbor, N.Y. (1989), which is hereby incorporated by reference). Typically, radiation is used to induce DNA damage. In cells that have just completed DNA synthesis but have not yet divided, repair of the damage leads infrequently to homologous chromosome exchange. If the homologous chromosomes are appropriately marked, the resultant recombination event can be scored in daughter cells. More recently, high-frequency homologous chromosome exchange has been achieved by the use of the yeast FLP/FRT system (Golic K., *Science*, 252, 958 (1991); Golic, K. and Lindquist, S. *Cell*, 59, 499 (1989); Harrison, D. and Perrimon, N., *Curr. Biol.*, 3, 424 (1993); Xu, T. and Rubin, G., *Development*, 117, 1223 (1993), which are hereby incorporated by reference). The FLP gene product is a site specific recombinase that catalyzes recombination at FRT target DNA elements. Expression in flies of FLP induces recombination between FRT elements on homologous chromosomes (Harrison, D. and Perrimon, N., *Curr. Biol.*, 3, 424 (1993); Xu, T. and Rubin, G., *Development*, 117, 1223 (1993), which are hereby incorporated by reference). Inducible control of FLP by a heat shock promoter has been used in flies to grade the extent or recombination, thus modulating the extent of genetic mosaicism (Xu, T. and Rubin, G., *Development*, 117, 1223 (1993), which is hereby incorporated by reference).

Genetic mosaics in flies have also been generated by inducing intramolecular chromosomal recombination with the FLP/FRT system. In one example of this strategy, a transgene is constructed such that it is inactivated by the insertion of a DNA sequence encoding a stop codon flanked by FRT sites. After induction of FLP the inactivating DNA cassette is 'flipped-out' allowing for the transcription of an mRNA that yields a translatable gene product (Struhl, G., Fitzgerald, K. and Greenwald, I., *Cell*, 73, 1323 (1993), which is hereby incorporated by reference). This approach could be used to generate gains or loss of function at any transcriptionally active transgene integration site or at a specific gene location targeted by homologous recombination.

Although the use of the FLP/FRT system in mammalian cells has been reported (O'Gorman, S., Fox, D. and Wahl, G., *Science*, 251, 1351 (1991), which is hereby incorporated by reference), a different recombination system, cre/loxP, has received wider attention and apparently greater success. The cre recombinase is bacteriophage P1-derived, and it interacts with its target site, loxP, a 34 bp element to produce site specific recombination (Sauer, B. and Henderson, N., *Proc. Natl. Acad. Sci. USA* 85, 5166 (1988); Sternberg, N. and Hamilton, D., *J. Mol. Biol.*, 150, 467 (1981), which are hereby incorporated by reference). Using a binary approach in transgenic animals, investigators constructed and introduced separately into the germline of mice two different transgenes; the first, a strong promoter driving cre, and the second a recombinatorial substrate which constrained two loxP sites (Lasko, M., et al., *Proc. Natl. Acad. Sci. USA*, 89, 6232 (1992); Orban, P., Chiu, D. and Marth, J., *Proc. Natl. Acad. Sci. USA*, 89, 6861 (1992), which are hereby incorporated by reference). Crossing the two transgenic lines gave rise to compound heterozygotes in which recombination occurred in a highly efficient manner. The cre/loxP system has also been applied in embryonic stem (ES) cells to create deleted alleles by targeting a homologous locus with a construct that contains loxP elements flanking the region to be excised (Gu, H., Zou, Y.-R. and Rajewsky, K., *Cell*, 73, 1155 (1993), which is hereby incorporated by reference). With this approach the transient expression of cre produced a significant frequency of recombination events (Gu, H., Zou, Y.-R. and Rajewsky, K., *Cell*, 73, 1155 (1993), which is hereby incorporated by reference). Overall, the use of recombination systems in mice appears to satisfy the need for the efficient creation of stable genetic mosaics. However, the approach is significantly limited by constraints imposed by the characteristics of the promoter chosen to express the recombinase. Since every cell that expresses the recombinase will likely suffer a recombination event, it is difficult to use the system to generate mosaic tissues.

A need exists for a system to produce stable genetic mosaics where precise temporal and spatial control of gene expression can be obtained.

SUMMARY OF THE INVENTION

The present invention relates to DNA molecules having recombinatorial substrates which can be activated to effect a gain or loss of function of a gene within the DNA molecule.

One aspect of the present invention relates to a DNA molecule encoding a recombinatorial substrate having (1) a promoter element capable of promoting transcription of genes in the recombinatorial substrate, (2) a gene whose expression is to be controlled, which is positioned 3' to the promoter element to facilitate its transcription, (3) a terminator positioned 3' to the promoter element and 5' to the gene whose expression is to be controlled to prevent transcription of the genes 3' to the terminator, and (4) two recombination sites located 3' and 5' to the terminator. The recombinatorial substrate is arranged such that treatment of the DNA molecule with a recombinase specific to the recombination sites removes the terminator from the DNA molecule, thus activating the recombinatorial substrate and permitting transcription of the gene whose expression is to be controlled.

Another aspect of the invention is a method of producing a transgenic mammal whose somatic and germ cells contain the recombinatorial substrate which, when treated by recombinase, transcription of the gene whose expression is to be controlled occurs. This recombinatorial substrate is introduced into an embryo which is then transplanted into a pseudopregnant mammal. The resulting transplanted embryo is allowed to develop to term. A mammal which carries the recombinatorial substrate is identified.

Another aspect of the invention is a method of activating the recombinatorial substrate which, when treated by recombinase, permits transcription of the gene whose expression is to be controlled. A recombinase is introduced into a transgenic mammal, causing this recombinatorial substrate to excise the terminator between the recombination sites. A mammal containing an activated recombinatorial substrate is then identified.

Yet another aspect of the invention is a DNA molecule encoding a recombinatorial substrate having (1) a promoter element capable of promoting transcription of genes in the recombinatorial substrate, (2) a gene whose expression is to be controlled, the gene being positioned 3' to the promoter element to facilitate its transcription, and (3) two recombination sites located 3' and 5' to the gene whose expression is to be controlled. The recombinatorial substrate is arranged such that treatment of the DNA molecule with a recombinase specific to the recombination sites removes the gene whose expression is to be controlled from the DNA molecule, thereby activating the recombinatorial substrate and resulting in the loss of function of the gene whose expression is to be controlled.

A further aspect of the invention is a method of producing a transgenic mammal whose somatic and germ cells contain a recombinatorial substrate which, when treated by recombinase, permits excision of the gene whose expression is to be controlled. This recombinatorial substrate is introduced into an embryonal stem cell which is integrated into a blastocyst which is then transplanted into a pseudopregnant mammal. The resulting transplanted embryo is allowed to develop to term. A mammal which carries the recombinatorial substrate is identified.

Another aspect of the invention is a method of activating the recombinatorial substrate which, when treated by recombinase, permits excision of the gene whose expression is to be controlled. A transgenic mammal, carrying this recombinatorial substrate is treated with a recombinase to excise the gene whose expression is to be controlled thereby activating the recombinatorial substrate and resulting in a loss of function of the gene whose expression is to be controlled. A mammal which contains an activated recombinatorial substrate is then identified.

BRIEF DESCRIPTION OF THE DRAWINGS

FIG. 1 shows a diagram of a recombinatorial substrate which activates the gene to be controlled and depicts a recombinatorial which when activated results in the loss of function of the gene to be controlled.

FIG. 2A is a diagram of NGF-XAT before and after cre-mediated recombination. NGF-XAT was transformed into $E.$ $coli$ that either did not express (FIG. 2B and 2C, lanes 1–9) or did express are recombinase (lanes 11–22). Plasmid DNA was isolated, digested and hybridized to the probes indicated in FIG. 2A.

FIG. 3A is a diagram of the NGF-XAT recombinatorial substrate and the expected short MRNA product. Northern hybridization of PolyA RNA with an NGF-XAT probe isolated from adult trangenic mice that is probed with an NGF-XAT probe. FIG. 3B demonstrates expression if the short NGF-XAT mRNA in two of the lines of transgenic mice with the NGF-XAT construct.

FIG. 4A uses an antisense probe and low power view encompassing the cortex, hippocampus and part of the thalamus. The CA1 and CA3 pyramidal and dentate gyrus regions of the hippocampus are labeled. FIG. 4B uses an antisense probe with high power view (boxed area in 4A) of dentate gyrus and pyramidal cell labeling. FIG. 4C uses a sense probe and low power view of encompassing cortex, hippocampus and part of the thalamus.

FIG. 5A is a diagram of HSVcre. FIG. 5B is a western blot of protein extracts isolated form NIH3T3 cells infected with HSVcre. FIG. 5C is a depiction of the NGF-XAT construct before and after recombination showing the location of the PCR primers. FIG. 5D is a PCR-Southern analysis to monitor CRE recombination in vivo. FIG. 5E is a nested PCR analysis to monitor recombination.

FIG. 6B is the histochemistry of the injection region using HSVlac. FIGS. 6A and 6C are regions anterior and posterior to the injection site.

FIG. 8 is a graph of the horizontal and vertical activity counts for each five minute interval for HSVcrelac and HSVlac mice.

DETAILED DESCRIPTION OF THE INVENTION

The study of gene product function in a varied organ systems has been facilitated by somatic mosaic analysis, whereby stable somatic mutations that result in either gain or loss of function are created and which allow for analysis of phenotypes among groups of cells genotypically identical except for the generated mutation. Ashburner, M., *Drosophila: A laboratory handbook* (1989), which is hereby incorporated by reference. To develop a related approach in mammals allowing for the production of focal and stable genetic changes in the postnatal animal, this invention provides a combined binary somatic and germline gene transfer strategy.

One aspect of the present invention relates to a recombinatorial substrate and its use, where activation of the substrate causes a gain of function by permitting expression of a gene in the substrate. This aspect of the present invention utilizes a DNA molecule encoding a recombinatorial substrate having (1) a promoter element capable of promoting transcription of genes in the recombinatorial substrate, (2) a gene whose expression is to be controlled, which is positioned 3' to the promoter element to facilitate its transcription, (3) a terminator positioned 3' to the promoter and 5' to the gene whose expression is to be controlled to prevent transcription of genes 3' to the terminator, and (4) two recombination sites located 3' and 5' to the terminator. The recombinatorial substrate is arranged such that treatment of the DNA molecule with a recombinase specific to the recombination sites removes the terminator from the DNA molecule, thus activating the recombinatorial substrate and permitting transcription of said gene whose expression is to be controlled.

Figure 1A:
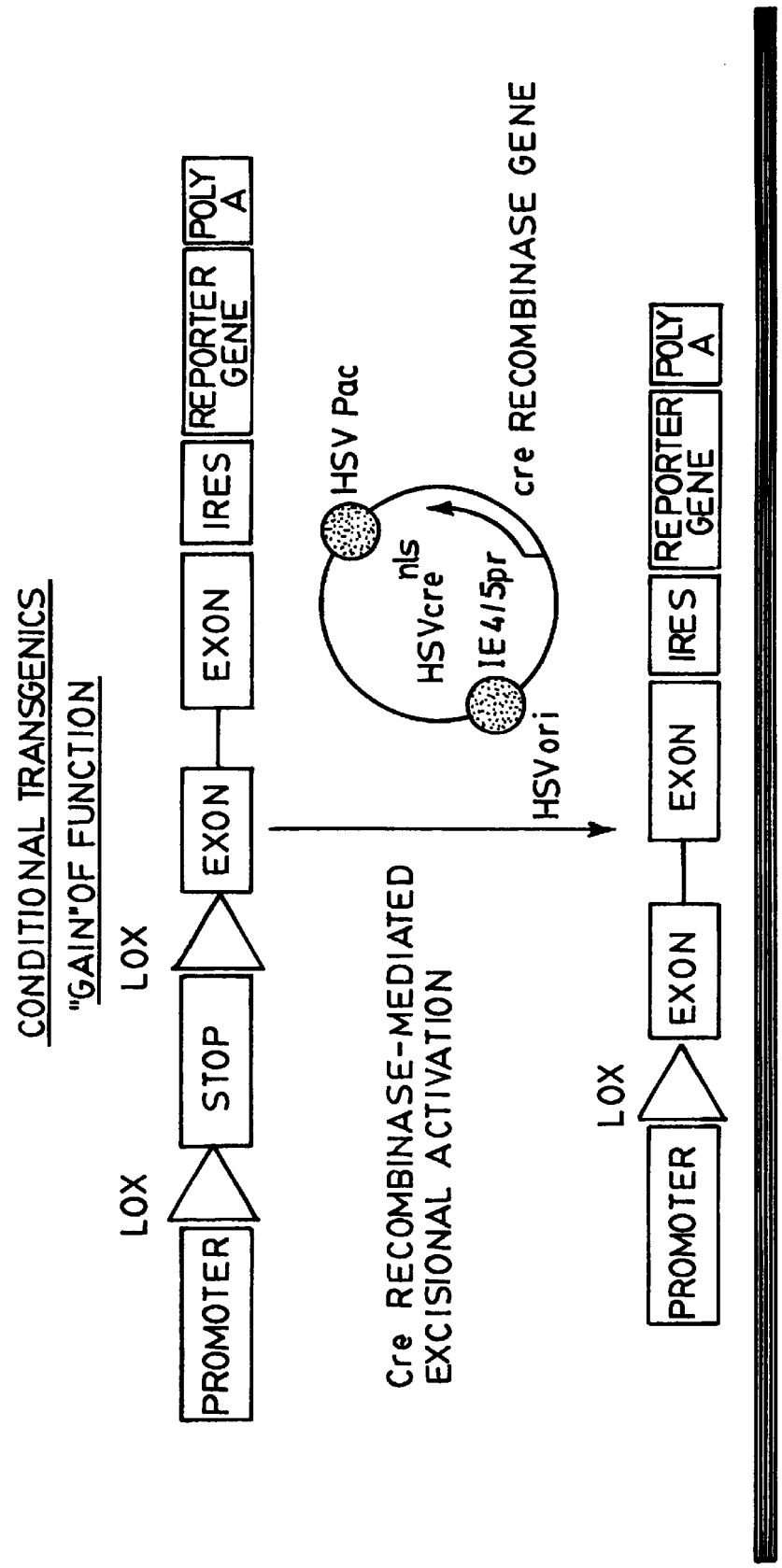
FIG. 1 summarizes the structure and use of recombinatorial substrates.
Figure 1B:
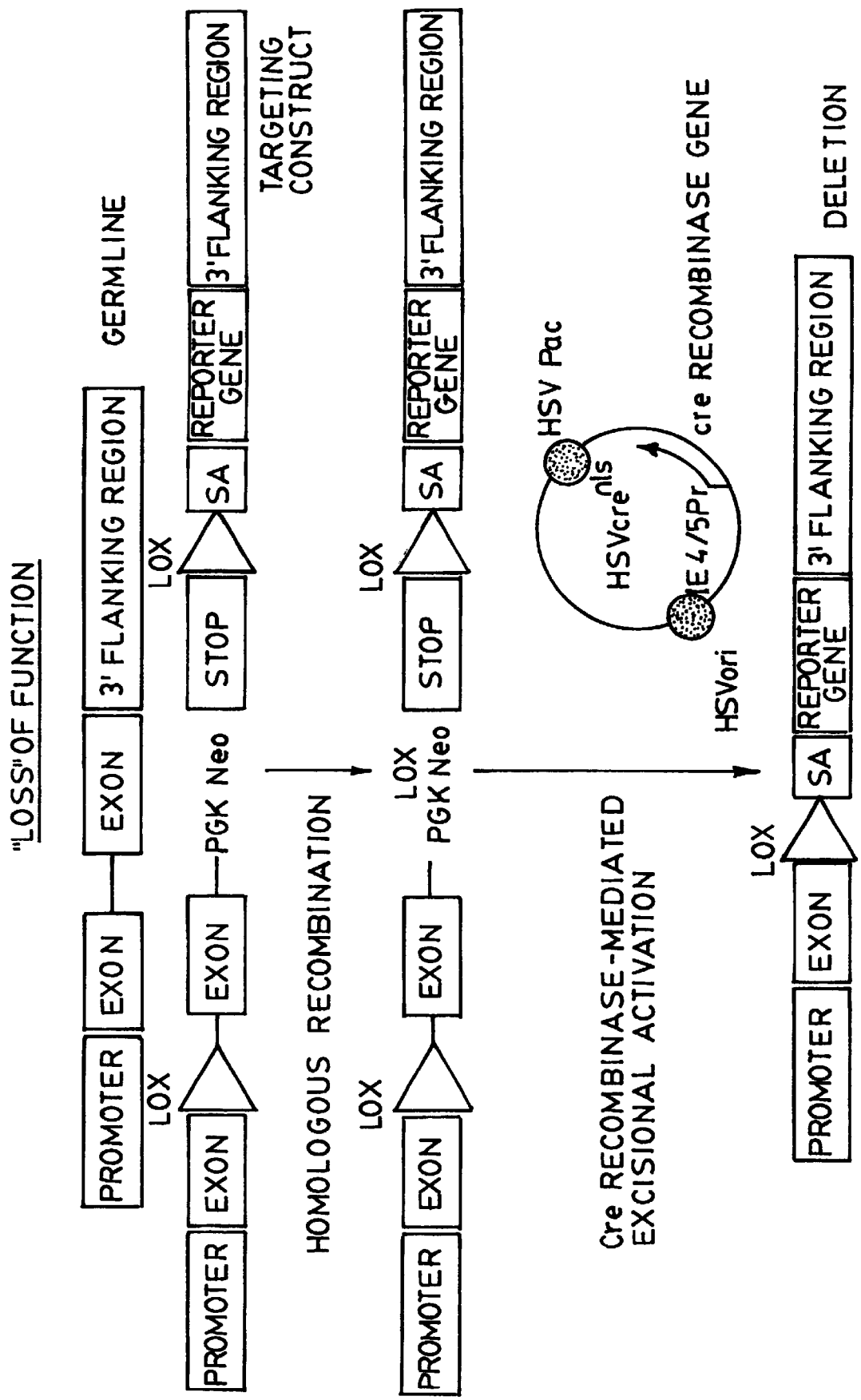

FIG. 1 depicts an example of such a DNA molecule before and after activation. The recombinatorial substrate prior to recombination has a promoter. Following the promoter, a stop, i.e. terminator, is located between two recombinase specific recombination sites. In the example in FIG. 1 the recombinatorial sites are LOX sites. The gene to be controlled is represented by the Exons. A reporter gene is located downstream followed by a polyA region, a 3' flanking region to stabilize the transcript. The recombinatorial substrate is then activated by a recombinase. In the example depicted, the recombinase is introduced on a herpes simplex virus. The activated recombinatorial substrate is shown, where the region between the LOX sites has been deleted. This results in the expression of the gene whose expression is to be controlled and the reporter gene.

Yet another aspect of the invention relates to a recombinatorial substrate and its use where activation of the substrates causes a loss of function by precluding expression of the gene whose expression is to be controlled by activating recombination sites surrounding the gene thereby deleting the gene. A further aspect of the present invention utilizes a DNA molecule encoding a recombinatorial substrate having (1) a promoter element capable of promoting transcription of genes in the recombinatorial substrate, (2) a gene whose expression is to be controlled, the gene being positioned 3' to the promoter element to facilitate its transcription, and (3) two recombination sites located 3' and 5' to the gene whose expression is to be controlled. The recombinatorial substrate is arranged such that treatment of the DNA molecule with a recombinase specific to the recombination sites removes the gene whose expression is to be controlled from the DNA molecule, thereby activating the recombinatorial substrate and resulting in the loss of function of the gene whose expression is to be controlled.

FIG. 1 depicts a recombinatorial substrate which when activated results in the loss of function of the gene whose expression is to be controlled. The gene in the germline has a promoter, followed by the exons coding for the gene product, and a 3' flanking region. The recombinatorial substrate is constructed with recombination sites on each side of the gene such that when recombination occurs the gene is inactivated. In the example depicted in FIG. 1, the recombinatorial substrate also has a terminator, or stop, located between the recombination sites. A reporter gene is located 3' to the terminator and when the substrate is activated the reporter gene is transcriptionally activated allowing for facilitated identification of activated recombinatorial substrates. FIG. 1 also identifies the recombination sites as LOX sites, a preferred embodiment of the invention. The recombinatorial substrate is introduced into the germline of the organism through homologous recombination as depicted in FIG. 1. The recombinatorial substrate can then be activated by introducing recombinase into the cells of the mammal. In FIG. 1, the recombinase is introduced via a herpes simplex virus. The activated substrate is shown at the bottom of FIG. 1 after recombination. The region between the recombination sites is deleted leaving only one copy of the recombination site. The loss of the gene between the recombination sites results in the loss of function of that gene in the mammalian cells where the substrate is activated.

To facilitate the identification of cells which carry an activated recombinatorial substrate, a reporter gene can be placed 3' to the terminator and the recombination sites. The reporter gene produces either an RNA or peptide which can be readily detected. Preferred reporter genes include the genes encoding LacZ, chloramphenicol acetyl transferase, luciferase, the green fluorescent protein, human alkaline phosphatase, hygromy unresistor gene; and neomycin phospho transferase.

The DNA molecule may also consist of a 3' flanking region which will stabilize the transcript made by the molecule and terminate transcription coming from the molecule, located 3' to the gene to be expressed. (Moreira, A., Wollerton, M., Monks, J., Proudfoot, N.J., *EMBO J.*, 14, 3809 (1995), which is hereby incorporated by reference) The 3' flanking region contains a transcription terminator and stabilizing elements such as a polyA region. Therefore, the 3' flanking region will be located where the transcript will terminate. The preferred 3' flanking sequences include the 3' flanking regions from the genes encoding β-galactosidase, SV40, β-globin, α-globin, and human growth hormone. The most preferred 3' flanking sequence is a 3' flanking sequence from a human growth hormone gene.

The preferred promoter elements include promoters from the genes encoding: myosin heavy chain α, myosin heavy chain β, insulin, somatostatin, glucagon, growth associated protein 43 kDa, superior cervical ganglion clone 10, neurofilament-L, neurofilament-M, neurofilament-H, glial bifilary protein, P0, myelin associated glycoprotein, myelin basic protein, calcitonin-gene related peptide, and a neuron specific enolase. The most preferred promoter element is a neuron specific enolase promoter.

The preferred recombinase sites include FRT and LoxP sites. The most preferred recombinase sites are LoxP sites.

The preferred terminators include transcription terminators for gastrin, C2 complement, and β-globin. The most preferred terminator is a β-globin transcription terminator.

This approach has broad application to the regulation of numerous genes. In particular this application is useful for creating and studying discrete modifications in genes where the spacial and temporal expression of the gene is important. Therefore, the genes to be controlled will include genes expressing regulatory factors, signal transducers, and developmental factors.

Although any gene may be used, the preferred genes whose expression is to be controlled includes genes expressing hormones, hormone receptors, neurotransmitters, neurotrophic factors, neurotrophic factor receptors, neuronal peptides, cell signaling molecules, and receptors for any of these peptides. The most preferred genes whose expression is to be controlled includes genes expressing neuronal growth factors.

The present invention also relates to any vectors which contain the recombinatorial substrates. Vectors include viral and plasmid vectors. Generally, this involves inserting the selected DNA molecule into an expression system to which that DNA molecule is heterologous (i.e. not normally present). The heterologous DNA molecule is inserted into the expression system or vector in proper orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccina virus. Recombinant viruses can be generated by transfection of plasmids into cells infected with virus.

Suitable vectors include, but are not limited to, the following viral vectors such as lambda vector systems gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS +/− (see "Stratagene Cloning Systems" Catalog (1993) from Stratagene, La Jolla, Calif., which is hereby incorporated by reference), pQE, pIH821, pGEX, pET series (see F. W. Studier et al., "Use of T7 RNA Polymerase to Direct Expression of Cloned Genes," *Gene Expression Technology* vol. 185 (1990), which is hereby incorporated by reference) and any derivatives thereof. Recombinant molecules can be introduced into cells via transformation, particularly transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA (mRNA) translation).

Transcription of DNA is dependent upon the presence of a promoter which is a DNA sequence that directs the binding of RNA polymerase and thereby promoted mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno (SD) sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of MRNA to ribosomes by duplexing with the rRNA to allow correct positioning of the ribosomes. For a review of maximizing gene expression, see Roberts and Lauer, *Methods in Enzymology*, 68:473 (1979), which is hereby incorporated by reference.

The present invention also includes any host cells carrying the recombinatorial substrate. Host cells include bacterial or animal cells, which may be used to maintain or propagate the recombinatorial substrate. Host cells also encompass mammalian cells which have been transformed with the recombinatorial substrate.

The present invention also provides for trangenic animals whose somatic and germ cells contain a recombinatorial substrate. One means available for producing a transgenic animal (e.g., a mouse)is as follows: Female mice are mated, and the resulting fertilized eggs are dissected out of their oviducts. The eggs are stored in an appropriate medium such as M2 medium (Hogan B. et al. Manipulating the Mouse Embryo, A Laboratory Manual, Cold Spring Harbor Laboratory (1986), which is hereby incorporated by reference). DNA or cDNA encoding gene, minigene or a recombinatorial substrate is purified from a vector (such as plasmids pCEXV-alpha [1a], pCEXV-alpha [1b], or pCEXV-alpha [1c]) by methods well known in the art. Inducible promoters may be fused with the coding region of the DNA to provide an experimental means to regulate expression of the transgene. Alternatively or in addition, tissue specific regulatory elements may be fused with the coding region to permit tissue-specific expression of the transgene. The DNA, in an appropriately buffered solution, is put into a microinjection needle (which may be made from capillary tubing using a pipet puller), and the egg to be injected is put in a depression slide. The needle is inserted into the pronucleus of the egg, and the DNA solution is injected. The injected egg is then transferred into the oviduct of a pseudopregnant mouse (i.e., a mouse stimulated by the appropriate hormones to maintain pregnancy but which is not actually pregnant), where it proceeds to the uterus, implants, and develops to term. As noted below, microinjection is not the only method for inserting DNA into the egg cell, and is used here only for exemplary purposes.

A preferred embodiment of the invention is where the transgenic mammal is selected from a mouse, rat, goat, cow or a pig. The most preferred embodiment is where the mammal is a mouse.

The invention also encompasses a cell line, clone, or tumor derived from a transgenic mammal which contains a recombinatorial substrate. In particular, the invention includes an embryonal stem cell clone which contains a recombinatorial substrate.

Another aspect of the invention is a method of producing a transgenic mammal whose somatic and germ cells contain a recombinatorial substrate. A recombinatorial substrate, which when treated with a recombinase specific to the recombination sites (a) removes the terminator from the DNA molecule, thus permitting transcription of said gene whose expression is to be controlled, or (b) removes said gene whose expression is to be controlled from said DNA molecule, thereby resulting in the loss of function of said gene whose expression is to be controlled, is introduced into an embryo. The embryo is then transplanted into a pseudopregnant mammal, and the transplanted embryo is allowed to develop to term. A mammal which carries the recombinatorial substrate is identified.

The introducing step may be carried out by microinjection or by introducing the DNA molecule into a blastocyst of an embryo or into embryonic stem cells.

A further embodiment of the invention relates to a method of obtaining mice which are homozygous for the recombinatorial substrate. Mammals carrying the recombinatorial substrate are interbred and a progeny mammal which carries the recombinatorial substrate on two alleles is identified.

A preferred embodiment of the invention is where mammals carrying the recombinatorial substrate are identified by identifying mammals which carry a reporter gene contained in the recombinatorial substrate. The identifying may be carried out by screening for a protein expressed by the reporter gene. For example, by using antibodies specific to the protein which is expressed. The antibodies may be chemically or radioactively tagged to facilitate detection. The identifying may also be carried out by screening for a phenotype conferred by the reporter gene. An example would be screening for drug resistance or fluorescence. The identifying may be further carried out by directly screening for the reporter gene or an RNA molecule made by the reporter gene using nucleic acid hybridization techniques.

Yet another aspect of the invention is a method of activating the recombinatorial substrate. Recombinase is introduced into a transgenic mammal, carrying the recombinatorial substrate, which when treated with a recombinase specific to the recombination sites (a) removes the terminator from the DNA molecule, thus permitting transcription of said gene whose expression is to be controlled, or (b) removes said gene whose expression is to be controlled from said DNA molecule, thereby resulting in the loss of function of said gene whose expression is to be controlled. A mammal which contains an activated recombinatorial substrate is then identified.

The recombinase may be introduced into the cells of the transgenic mammal by a number of delivery methods including chemical or physical methods and via vectors. Preferred chemical and physical methods of delivery include using virosomes, liposomes, naked DNA and particle bombardment, sometimes known as the gene gun.

A preferred approach is to introduce a nucleic acid coding for the recombinase through the use of viral vectors. Viral vectors have the potential of achieving regional gene expression in organotypic slice cultures and in vivo. The preferred vectors include Adenovirus ("Ad") (Akli S. et al., *Nat. Genet* 3, 224 (1993); Bajocchi, G., Feldman, S., Crystal, R. and Mastrangeli, A., *Nat. Genet.*, 3, 229 (1993); Davidson, B., Allen E., Kozarsky, J., Wilson, K. and Roessler, B., *Nat. Genet.*, 3, 219, (1993); Le Gal La Salle, G. et al., *Science*, 259, 988 (1993) which are hereby incorporated by reference), adeno-associated virus ("AAV") (Kaplitt, M. et al., *Nat. Genet.*, 8, 148 (1994a) which is hereby incorporated by reference), and Herpes Simplex Virus ("HSV") (Dobson, A., Margolis, T. P., Sedarati, F., Stevens, J. and Feldman, L., *Neuron*, 5, 353 (1990); Federoff, H., Geller, A. and Lu, B., *Soc. Neurosci Abstr.*, 16, 353 (1990); Fink, D. et al., *Hum. Gene Ther.*, 4, 11, (1992); Geller, A., *Curr. Opin. Gen. Dev.*, 3, 81 (1993); Geller and Breakefield (1988); Geller, A. and Freese, A. *Proc. Natl. Acad. Sci. USA*, 87, 1149 (1990); Geschwind, M., Kessler, J., Geller, A. and Federoff, H., *Brain Res. Mol. Brain. Res.*, 27, 327 (1994); Ho, D., Mocarski, E. and Sapoloski, R., *Proc. Natl. Acad. Sci. USA*, 90, 3655 (1993); Kaplitt, M. et al., *Mol. Cell. Neurosci.*, 2, 320 (1991), *Proc. Natl. Acad. Sci. USA*, 91, 8979 (1994b), which are hereby incorporated by reference).

The most preferred virus is HSV, a 150 kb DNA virus that contains approx. 70 genes (Roizman, B., *Virology*, 2nd Edn., 1787 (1990), which is hereby incorporated by reference). HSV has a broad host range and appears to be capable of infecting most mammalian differentiated cell types. A number of genes within the wild-type HSV genome are dispensable for its growth in tissue culture. This was initially exploited by Roizman and his colleagues to develop recombinant HSV viruses as vehicles for the transfer of heterologous genes (Roizman, B., Jenkins, F. J., *Science*, 229, 1208 (1985); Roizman, B. and Sears, A., *Virology*, 2nd Edn., 1795 (1990), which are hereby incorporated by reference). Subsequently, this recombinant HSV vector approach has been used by a number of investigators and remains a viable gene transfer method that complements the HSV amplicon vector approach to be described (Andersen, J., Garber, D., Meaney, C. and Breakefield, X., *Hum. Gene. Ther.*, 3, 487 (1992); Dobson, A., Margolis, T. P., Sedarati, F., Stevens, J. and Feldman, L., *Neuron*, 5, 353(1990); Fink, D. et al., *Hum. Gene. Ther.*, 4, 11 (1992), which are hereby incorporated by reference).

The amplicon vector concept arose from analysis of the genomes of defective interfering HSV particles (Spaete, R. and Frenkel, N., *Cell*, 30, 305 (1982); Stow, N. and McManagle, E., Eucaryotic Viral Vectors, Cold Spring Harbor Laboratory Press, Cold Spring Harbor, N.Y., 199 (1982), which are hereby incorporated by reference) that accumulated in HSV stocks that were passaged at high multiplicities of infection. These genomes were composed of relatively simple reiterations of a subset of DNA sequences from the wild-type HSV genome. Principally, the genomes contained an origin of DNA replication ("ori") and a cleavage/packaging site ("pac") (Spaete, R. and Frenkel, N., *Cell*, 30, 305 (1982), Spaete, R. and Frenkel, N. *Proc. Natl. Acad. Sci. USA*, 82, 694 (1985); Stow, N. and McManagle, E., Eucaryotic Viral Vectors, Cold Spring Harbor Laboratory Press, Cold Spring Harbor, N.Y., 199 (1982), which are hereby incorporated by reference). When the ori and pac were cloned into a plasmid it could be replicated and packaged into virions when transfected into a cell and supplied with HSV replication and virion assembly functions by a superinfecting wild-type virus. Analysis of the genomes in these amplicon stocks indicated that the plasmid-derived sequences were predominantly 150 kb molecules composed of concentrated units of the original plasmid (Spaete, R. and Frenkel, N., *Cell*, 30, 305 (1982), Spaete, R. and Frenkel, N. *Proc. Natl. Acad. Sci. USA*, 82, 694 (1985); Stow, N. and McManagle, E., Eucaryotic Viral Vectors, Cold Spring Harbor Laboratory Press, Cold Spring Harbor, N.Y., 199 (1982); Vlazny, D., Kwong, A. and Frenkel, N. *Proc. Natl. Acad. Sci. USA*, 79, 1423 (1982), which are hereby incorporated by reference).

Production of amplicon vectors requires a co-propagated HSV helper virus. Most investigators use helper viruses that carry mutations in an essential immediate early ("IE") HSV gene, typically IE3 (Geller, A. and Freese, A., *Proc. Natl. Acad. Sci. USA,* 87, 1149 (1990); Paterson, T. and Everett, R. *J. Gen. Virol.,* 71, 1775 (1990), which are hereby incorporated by reference). Helper virus with a missense mutation within the IE3 gene have a temperature sensitive phenotype: replication occurs at 34° C. but not at 39° C. (Preston, C., *J. Gen. Virol.,* 71, 1775 (1979a), Preston C., *J. Virol.,* 29, 275, (1979b), which are hereby incorporated by reference). Deletion of all or part of the IE3 gene yields viruses that are incapable of growing on normal tissue culture cells but can be grown on cell lines that stably express integrated copies of the IE3 gene. These complementing cell lines have been generated in different cell types and with different transfected gene segments (DeLuca, N., McCarthy, A. and Schaffer, P., *J. Virol.,* 56, 558 (1985); DeLuca, N. and Schaffer, P., *Nucleic Acids Res.,* 15, 4491, (1987); Paterson, T. and Everett, R. *J. Gen. Virol.,* 71, 1775 (1990), which are hereby incorporated by reference). Helper virus carrying a partial deletion of the IE3 gene, when grown on a complementing cell line, results in the generation of recombinant wild-type particles. The frequency ($10^{-5}$–$10^{-6}$) at which such particles arise appears related to the extent of overlapping homology between the integrated gene and the residual IE3 sequences flanking the deletion in the helper virus genome (DeLuca, N., McCarthy, A. and Schaffer, P., *J. Virol.,* 56, 558 (1985); DeLuca, N. and Schaffer, P., *Nucleic Acids Res.,* 15, 4491, (1987); Paterson, T. and Everett, R. *J. Gen. Virol.,* 71, 1775 (1990), which are hereby incorporated by reference). Typical amplicon stocks will have titers between 1 and $10 \times 10^6$ infectious particles of amplicon and between 0.1 and $5 \times 10^7$ plague forming units of helper virus.

The typical amplicon vector contains: a plasmid backbone with a Col E1 origin and a drug resistance gene (typically β-lactamase) for growth in *E. coli;* a HSV origin of replication; a cleavage/packaging sequence; and a transcription unit. Initial amplicon vectors were constructed so that a viral promoter, usually an HSV IE promoter (Ho, D., Mocarski, E. and Sapoloski, R., *Proc. Natl. Acad. Sci. USA,* 90, 3655 (1993); Kaplitt, M. et al., *Mol. Cell. Neurosci.,* 2, 320 (1991), which are hereby incorporated by reference) were driving the expression of the gene of interest. Recently some investigators have begun to construct amplicon vectors with multiple genes (Geschwind, M., et al., *Hum. Gene Ther.,* 7, 173 (1996), which is hereby incorporated by reference), regulated promoters (Lu, B. and Federoff, H., *Hum. Gen. Ther.,* 6, 421 (1995), which is hereby incorporated by reference), and cellular promoters (Kaplitt, M., et al., *Nat. Genet.,* 1996, 8, 148 (1994a), which is hereby incorporated by reference) that are helpful in controlling the extent and specificity of gene expression.

Amplicon vectors can efficiently transfer genes into post-mitotic neurons in dissociated cell culture, organotypic slice culture and in the intact brain (Andersen, J., Garber, D., Meaney, C. and Breakefield, X., *Hum. Gene. Ther.,* 3, 487 (1992); Bergold P., Casaccia-Bonnefil, P., Federoff, H. and Stelzer, A. , *Soc. Neurosci. Abstr.,* 19, 21 (1993a), Bergold, P., Cassaccia-Bonnefil, P., Xiu-Liu, Z. and Federoff, H., *Proc. Natl. Acad. Sci. USA,* 90, 6165 (1993b); Dobson, A., Margolis, T. P., Sedarati, F., Stevens, J. and Feldman, L., *Neuron,* 5, 353 (1990); Federoff, H., Geller, A. and Lu, B. *Soc. Neurosci. Abstr.,* 16, 353 (1990), Federoff, H., Geschwind, M., Geller, A. and Kessler, J., *Proc. Natl. Acad. Sci. USA,* 89, 1636 (1992); Fink, D., et al., *Hum. Gene. Ther.,* 4, 11 (1992); Geller and Breakefield, 1988; Geller, A. and Freese, A., *Proc. Natl. Acad. Sci. USA,* 87, 1149 (1990); Geschwind, M., et al., *Hum. Gene Ther.,* 7, 173 (1996); Ho, D., Mocarski, E. and Sapoloski, R., *Proc. Natl. Acad. Sci. USA,* 90,3655 (1993); Huang, Q. et al., *Exp. Neurol.,* 115, 303 (1992); Kaplitt, M., et al., *Mol. Cell. Neurosci.,* 2, 320 (1991), Kaplitt, M., et al., *Nat. Genet.,* 8, 148 (1994a); Wolfe, J., Deshmane, S. and Fraser, N., *Nat. Genet.,* 1, 379 (1992), which are hereby incorporated by reference). Most data suggest that in vivo expression of transferred genes from amplicon vectors decline within a month (Federoff, unpublished data) although some studies report small numbers of expressing cells at a year (During, M., Naegele, J., O'Malley, K. and Geller, A., *Science,* 266, 1399 (1994), which is hereby incorporated by reference). In these studies, gene expression was driven by HSV promoters. It is unclear to what extent decreasing expression reflects loss of amplicon genomes, down-regulation of viral promotor transcription or both processes. Studies of viral promotor driven gene expression in different types of vectors suggest that down-regulation is a common problem, thus leading to the speculation that a similar mechanism operates in the amplicon vector.

To satisfy the requirement for spatial and temporal control of gene expression, amplicons need to be capable of producing regional infections of a slice culture and express with a predictable time course. Bath application of virus resulted in widespread gene transfer and expression predominantly in glia on the edge of slice cultures and little expression in neurons (Casaccia-Bonnefil, P., et al., *J. Neurosci. Methods,* 50, 341 (1993), which is hereby incorporated by reference). Using a micropipette to deliver nanoliter quantities of virus directly to regions of the slice culture produced regional infections. Analysis of gene product expression in such cultures showed that it was limited to the microapplication site. With this method, there is a linear relationship between the number of virions applied and the number of transduced cells (Casaccia-Bonnefil, P., et al., *J. Neurosci. Methods,* 50, 341 (1993), which is hereby incorporated by reference). Moreover, expression from the HSV IE 4/5 promoter in the amplicons was activated rapidly, within 4 h after virus microapplication (Casaccia-Bonnefil, P., et al., *J. Neurosci. Methods,* 50, 341 (1993), which is hereby incorporated by reference).

For this invention any site specific recombinase which can promote recombination in mammals can be used. The preferred recombinases include FLP from yeast and cre. The most preferred recombinase is cre.

In the examples below, a somatic mosaic approach has been developed for a mouse whereby a dormant germline transgene is activated by the somatic delivery and expression of cre recombinase. Transgenic mice harboring a recombinatorial substrate, the germline transmitted nerve growth factor excision activation transgene (NGF-XAT), were generated. Somatic delivery of virus vectors expressing cre recombinase into the brain of NGF-XAT mice resulted in regional recombination and activation of the transgene as demonstrated at the DNA level by PCR and at the protein level by both immunocytochemistry and ELISA. This approach has been exploited to evaluate a behavioral correlation of unilateral NGF mosaicism within the dorsal hippocampal formation. NGF-XAT mice activated by expression of cre recombinase manifest increased locomotor activity compared to NGF-XAT mice transduced by a control virus expressing *E. coli* β-galactosidase. The following non-limiting examples show that focally increased expression of NGF in one part of a synaptic network can elicit changes in behavior presumably by altering the overall function of NGF-responsive neural circuitry.

EXAMPLES

Example 1

Experimental Protocols

Northern Blot Analysis of Total Brain mRNA From NGF XAT Transgenic Lines

The NGF-XAT was excised from pBS and injected into the pronuclei of fertilized eggs, cultured briefly and transferred into the oviduct of psuedopregant females. Six founders were obtained. Poly A+ RNA was prepared from adult mice of five independent transgenic lines (#s 30, 2, 25, 3 and 10) by the Fast Track Kit (In Vitrogen, Torrence, Calif.). Approximately 2 µg of RNA of each were fractionated on a 1.2% agarose gel containing formaldehyde. The gel was blotted to a nylon membrane, prehybridized and then hybridized to a $^{32}$P labeled probe. The blot was washed under stringent conditions and exposed to film for 14 hours. Because the probe contains approximately 90 bp complementary to the 5' UTR of the endogenous NSE mRNA, it serves also as an internal control for RNA loading.

Nested PCR & Southern Blot Analysis

All PCR reactions were completed using a modified buffer containing 50 mM TrisHCl pH 9.0, 16 mM $(NH_4)_2SO_4$, 2.25 mM $MgCl_2$, 2% DMSO, and 0.1% Tween-20. One µg of genomic DNA, 1 nM of each oligonucleotide, 50 µm DNTP's (Boehringer), and 1 µl of Taq Polymerase (Perkin-elmer) was added to each 100 µl reaction. Sense primer 1 (5' GCTCGTACGTGCGTCTCCGCCTGCAGCTCTE') and antisense primer 2 (5' AACGCTGTGATCAGAGTGTA 3') was subject to 40 cycles of PCR (Perkin-Elmer 9600) with an annealing temperature of 61° C. for 45 seconds and an extension time of 2 minutes at 72° C. One µl of each product was re-amplified using sense primer 3 (5' CATGCGCTCGCTCGGCTCTA 3') and antisense primer 4 (5 ' GACTCACCGATGCGCGTCCCCTCCGGCTCCA3'). The nested reaction was subjected to 40 cycles of PCR with an annealing temperature of 66° C. for 45 seconds and an extension time of 2 minutes at 72° C. Samples were electrophoresed on a 1% agarose gel and visualized by ethidium bromide fluorescence (Fotodyne). PCR product from primer pair 1/2 was electrophoresed on a 1% agarose gel and transferred to nylon membrane (MSI). The blot was prehybridized and then hybridized with $^{32}$p labeled Lox probe. A 123 bp loxP fragment was isolated from SK-lox with Pst 1 and labeled with $^{32}$P dCTP (S.A. 3000 Ci/mmol; Dupont). The blot was washed under stringent conditions and exposed to film for 7 hours.

Western Blot $10 \times 10^6$ 3T3 cells were plated on a 100 mm plate. The following day, cells were infected with approximately $1 \times 10^6$ infectious particles of HSVCre or HSVlac for 5 hours. The virus was removed, the cells were washed, and fresh media was added for 24 hours. The following day the media was removed and the cells were washed with 1× PBS and lysed with 0.5 ml of Laemmli buffer for 15 minutes on ice (Laemmli, U. Nature 227, 680 (1970), which is hereby incorporated by reference). 250 ng of lysate per well was run on a 4–20% gradient gel (Bio-Rad) with 15 µl of Low Molecular weight markers (Amersham) as size standards. The gel was run for 35 minutes at 100 volts. Transfer of the gel onto a nitrocellulose filter (Protran BA 83, S&S) was completed overnight. A 1/10,000 dilution of Cre antibody (generously provided by DuPont, Inc.) in 5% milk and PBS was added to the blot and incubated overnight at 40° C. The blot was developed following the ECL western blotting protocol using a secondary antibody recommended by the manufacturer (Amersham). The blot was exposed to film (XAR, Kodak) for 10–20 seconds and then developed.

Stereotaxic Injections

Mice were anesthetized with 3% halothane in 70% $N_2O$ and 30% $O_2$ in the induction anesthesia chamber and maintained at 2% halothane during stereotaxic intracerebral injections. After positioning in a Kopf stereotaxic apparatus, the skull was exposed via a midline incision and burr holes were drilled. The coordinates, relative to Bregma, for NGF immunocytochemistry were −2.0 mm, lateral 2.5 mm, and deep 1.8 mm; and those for the behavioral studies were −2.0 mm, lateral 1.5 mm and deep 1.5 mm. A 33 GA needle was gradually advanced to the desired depth and 2–3 µl (approximately $10^5$ infectious particles) were slowly infused over the time course of 5 minutes. Four days later, half of the mice were killed by halothane overdose for X-gal staining. Fourteen days later the remaining mice were prepared for β-NGF immunocytochemistry.

X-gal Staining

Frozen sections (20 µm) from HSVcrelac and HSVlac injected animals were mounted on subbed slides and stored at −20° C. Sections were post-fixed for five minutes with 1% glutaraldehyde. Slides were washed three times with 1×PBS and submerged in a solution containing: 5 mM potassium Ferricyanide, 5 mM potassium ferrocyanide, 0.02% NP-40, 0.01% sodium deoxycholate, 2 mM $MgCl_2$ and 1 µg of X-Gal (Gibco). Slides were incubated overnight at 37° C. and counterstained with thionin for three minutes. After staining sections were dehydrated and coverslipped as described in the β-NGF immunostaining method.

β-NGF Immunocytochemistry

Adult mice were anesthetized with 3.0% halothane in 70% $N_2O$ and 30% $O_2$ using a Fluotec 3 vaporizer (Colonial Medica, Amherst, N.H.). A 24 GA angiocatheter (Angiocath, Deseret Medical Inc., Sandy, Utah) was placed into the apex of the left ventricle and intracardiac perfusion was initiated with 10 ml of heparinized saline (5,000 U/liter saline) followed by 20 ml of chilled solution of 2% paraformaldehyde in 0.075 M phosphate buffer (pH=7.5, Mallinckrodt UN 2213) in 0.2% parabenzoquinone. Brains were extracted and postfixed in paraformaldehyde-parabenzoquinone solution for additional 2–3 hrs at 4 C. Following that, the brains were placed into 10 ml of a cryoprotective solution of ethylene glycol (30%) and sucrose (20%) in 0.1 M phosphate buffer (pH=7.5) for 24 hrs. Forty micron serial sections were cut on powdered dry ice using an American Optical sliding microtome and stored in phosphate buffer containing 0.06% azide at +4° C. until processed for β-NGF immunocytochemistry. Representative coronal sections of the mouse brains were placed into Costar net wells (VWR) and incubated for 10 min in 0.1 M Tris buffered saline (pH=7.6) followed by 2 consecutive 10 minutes washes in TBS with 0.25% Triton (T-8787, Sigma). Blocking was performed for 60 min in a solution of 2% crystalline grade bovine serum albumin (A-8022, Sigma) and 5% normal goat serum in TBS followed by a brief 5 min wash in 0.25% Triton solution of TBS. Staining with rabbit polyclonal (affinity purified) antibodies to mouse β-NGF (1:1000 dilution or 1 µg/ml) was performed for 60–64 hrs as recommended by Conner et al, Muir, D., Varion, S., Hagg, T. and Manthorpe, M. J Comp Neurol 319, 454 (1992) (which is hereby incorporated by reference) at +4 C. Bound antibodies were detected by incubating sections in 1.5 µg/ml of biotinylated goat anti-rabbit antibody (Vectastain Elite, rabbit IgG ABC kit, PK-6101, Vector labs, Burlingame, Calif.) in a 0.25% triton solution of TBS with 0.5% goat serum for 3 hrs at room temperature. Sections were then incubated at room temperature for 90 min in the avidin-biotin-peroxidase reagent according to the manufacturer's recommendations.

After consecutive 10 minutes rinses in TBS and Tris-HCl the sections were placed for 7 min into a filtered solution of 0.04% diaminobenzidine (D-5637, Sigma), 0.06% nickel chloride (N 5756, Sigma) and 0.06% hydrogen peroxide in 0.1 M Tris HCl buffer (pH 7.4). Sections were then rinsed in phosphate buffer, mounted with a fine paintbrush on superfrost coated slides (Fisher), dehydrated in 95% and 100% alcohols, incubated in histological grade xylene, coverslipped with permount, and left to dry for 24 hrs.

NGF ELISA

Brain regions containing the injection site were surgically isolated from the animals injected with either HSVcrelac and HSVlac. They were extracted in buffer containing PBS, 0.4 M NaCl, 0.05% Tween 20, 0.5% BSA, 0.1 mM benzethonium chloride, 1 mM PMSF, and 3.5 $\mu$g/ml of aprotinin in a 1:1 weight/volume proportion. The samples were homogenized in a micro glass tissue grinder (Wheaton). Samples were then subjected to five rounds of cup sonication at 40% output power. Homogenates were centrifuged at 16,000×g at 4° C. for 60 minutes. Supernatants were diluted serially with a buffer containing 50 mM Tris-HCl, 200 mM NaCl, 10 mM $CaCl_2$, 1% BSA, 0.1% Triton X-100 and 0.1% sodium azide and added to High Binding ELISA plates (Costar) that are prepared as follows. ELISA plates were coated with a 1 $\mu$g/ml solution of anti-rhNGF (generously supplied by Dr. Dominick Sinicropi), incubated for 2 hours at 37° C. and then blocked for 1 hour at 37° C. Supernatants and murine NGF standards were added and incubated overnight at 4° C. Anti-NGF-$\beta$gal conjugate (Boehringer Mannheim) was added for four hours at 37° C. and the assay developed according to the manufacturers protocol (Boehringer Mannheim). Samples were read at 595 nm (Bio-Rad) and a standard curve was derived from murine NGF controls. Brain samples for both HSVcrelac and HSVlac injected animals were measured against the standard curve.

In Situ Hybridization

In situ hybridization was performed on 12 $\mu$m coronal sections using the Boehringer Mannheim Digoxigenin labeling and detection system. Oligonucleotide probes (45 mer's) complementary to hGH Exon II were 3'-end labeled for 10 minutes and used in a 1:50 dilution. Frozen sections were brought to room temperature and fixed in 4% paraformaldehyde for 15 minutes. After fixation the sections were washed once in 1×PBS and incubated at room temperature in 2×SSC. Sections were then rinsed two times in 1×PBS and digested with proteinase K (20 $\mu$g/ml) at 37° C. for 20 minutes. Sections were postfixed in 4% paraformaldehyde for 5 minutes and then washed in PBS. Prior to prehybridization the sections were acetylated to decrease nonspecific binding of probe. Sections were incubated in triethanolamine and 0.5% acetic anhydride for 10 minutes followed by a 10 minutes wash in 2×SSC. Prehybridization buffer consisting of: 50% deionized formamide, 4×SSC, 1×Denhart's, 10% Dextran sulfate, 30 $\mu$g/ml salmon sperm DNA and 25 $\mu$g/ml yeast tRNA, was added to the sections and allowed to incubate at room temperature for one hour. After prehybridization sections were rinsed briefly in 2×SSC. Probe was denatured for 5 minutes at 95° C. and added to prehybridization solution in a 1:50 ratio and incubated overnight at 37° C. Sections were washed with increasingly stringent washes (SSC: 2×, 1×, 0.5×) first at room temperature and 37° C. over a period of 3 hours. Anti-digoxigenin was added in a 1:500 dilution to the sections in the presence of 1% sheep serum and 0.003% Triton X-100 and incubated at room temperature for 4 hours. After several Tris-HCl washes color detection solution was added (NBT & X-Phosphate) to the slides and they were developed overnight.

Locomotor Activity

Horizontal and vertical locomotor activity measurements were made in an automated device based on infra-red beam breaks (Opto-Varimex Minor, Columbus Instruments International Corporation) at 5 minute intervals over the course of a 90 minutes experimental session on a single day. Each beam was separated by 25.4 mm. with the width of each beam being 3 mm in diameter. Interruption of any horizontal or vertical beam generated an electrical impulse that was collected using the Opto-M data software. Horizontal beams registered only when the mouse moved in the horizontal plane of the test cage, and jumping and rearing were registered by the vertical beam. Statistical analyses were carried out using 2 way repeated measures analyses of variance with transgene as a between group variable and time interval as a within group variable (SuperANOVA, Abacus Concepts, Inc.).

Example 2

Design of a Germline Transmitted Recombinatorial Substrate

Figure 2A:
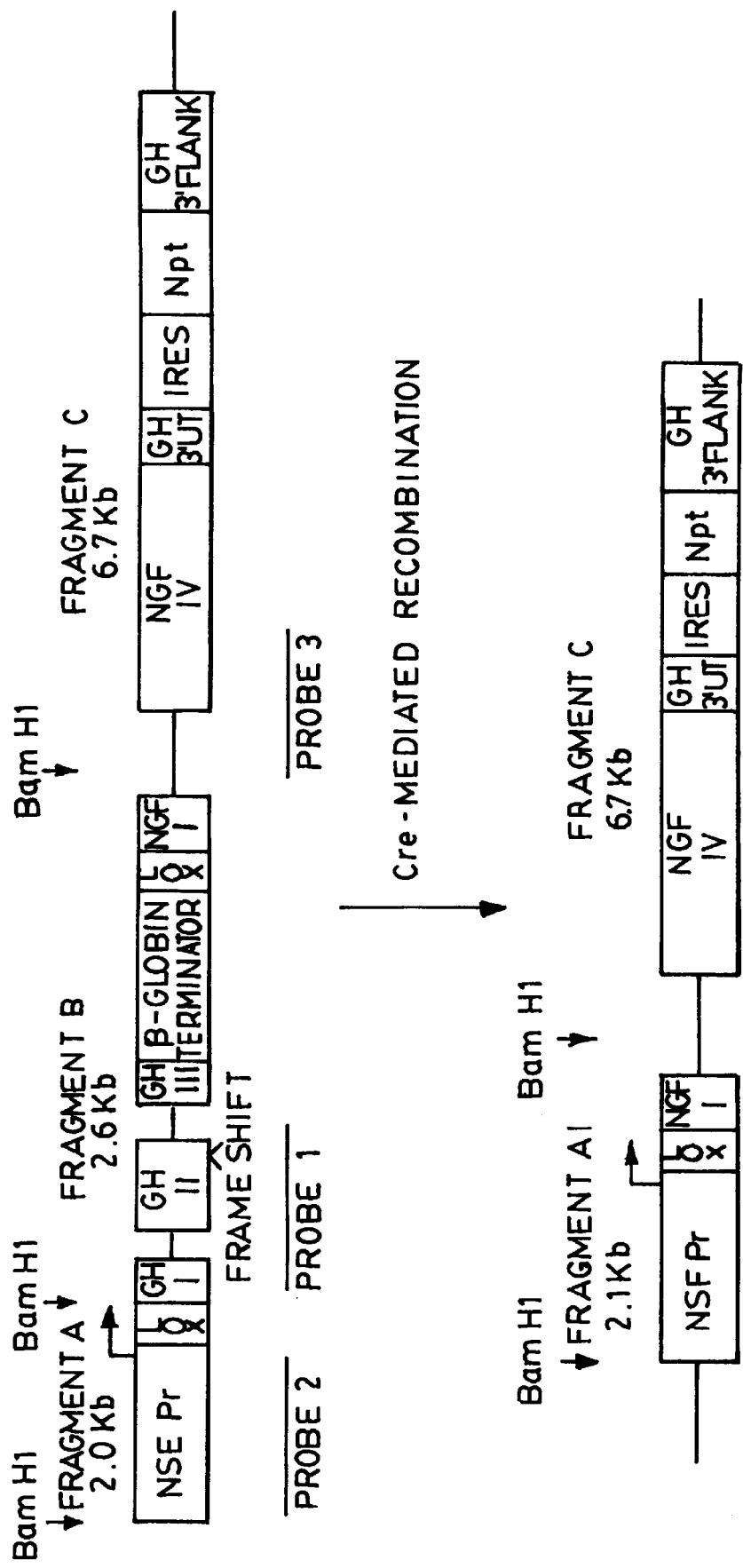
FIG. 2A–C shows the NGF-XAT construct and recombination driven excision.

A germline transmitted recombinatorial substrate, the NGF excisional activation transgene (NGF-XAT), was designed to synthesize a neuron-specific non-coding transcript that upon activation by somatically expressed cre recombinase an inactivating cassette is excised allowing for NGF expression. The NGF-XAT (FIG. 2A) is driven by the 1.8 kb neuron specific enolase ("NSE") promoter, contains a loxP bounded mutated fragment of the human growth hormone ("hGH") gene fused to the $\beta$-globin transcription terminator, the NGF mini-gene, and a IRES initiated neomycin phosphotransferase gene ("IRESNpt"), and 3' flanking sequence from hGH gene.

Example 3

Demonstration of Recombination Driven Excision in *E. coli*

Figure 2B:
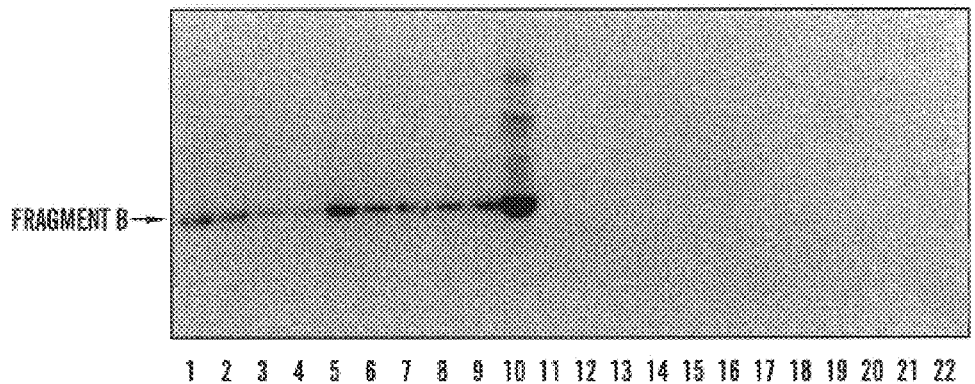
Figure 2C:
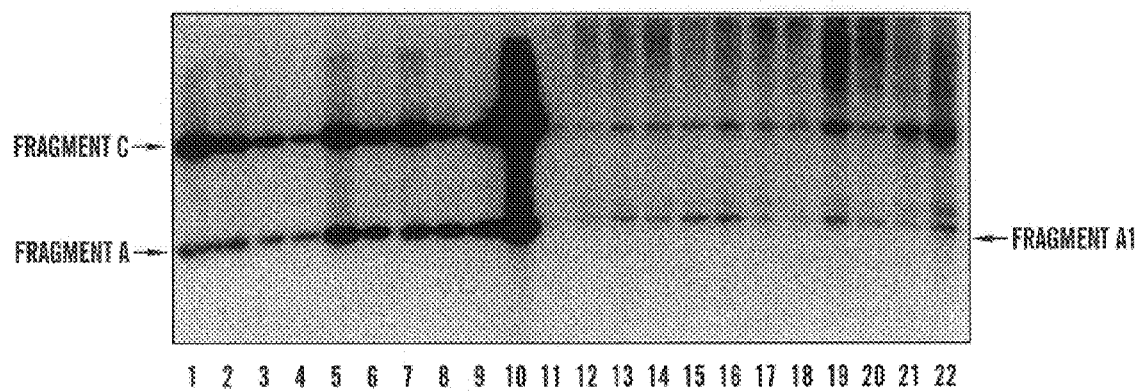

To demonstrate the efficiency and fidelity of excision of the inactivating cassette, the NGF-XAT was introduced into bacteria constitutively expressing the cre recombinase (FIGS. 2B and 2C, lanes 1–9) and also control bacteria lacking the recombinase (lanes 11–22). Plasmid miniprep DNA from independent transformants from both strains were prepared, digested with BamH1, size fractionated on an agarose gel, and Southern blotted. Southern blot analysis of the independent bacteria plasmids revealed highly efficient removal: all colonies lacked the restriction fragment corresponding to the inactivating cassette. A BamH1 digest of control NGF-XAT DNA was run in lane 10. The results are shown in FIG. 2B. In FIG. 2B, the blot was hybridized with probe (see FIG. 2A). Only plasmids prepared from bacteria lacking cre recombinase contained this fragment (Fragment B); all plasmids from bacteria expressing cre recombinase had deleted this fragment. In FIG. 2C the blot was hybridized to probes 2 and 3, demonstrating that the plasmids from both types of bacteria liberated the expected fragments (Fragments A, A1, and C). Fragment A1 is slightly larger than Fragment A because recombination creates a new 3' BamH1 site. Direct sequencing of the "collapsed" construct indicated removal of the cassette. By contrast, the intact NGF-XAT was recovered from all bacteria that did not express cre recombinase.

Example 4

Generation of Transgenic Mice

The NGF-XAT was excised from pBS, injected into the pronuclei of fertilized eggs, cultured briefly, and transferred into the oviduct of pseudopregnant females. Six founders were obtained. Poly A+RNA was prepared from adult mice of five independent transgenic lines (#s 30, 2, 25, 3 and 10) by the Fast Track Kit (In Vitrogen, Torrence, Calif.). Approximately 2 µg of RNA of each were fractionated on a 1.2% agarose gel containing formaldehyde. The gel was blotted to a nylon membrane, prehybridized and then hybridized to a $^{32}$P labeled probe (Northern Probe 1 in FIG. 3A). The blot was washed under stringent conditions and exposed to film for 14 hours (FIG. 3B). Because the probe contains approximately 90 bp complementary to the 5' UTR of the endogenous NSE mRNA, RNA loading was internally controlled.

Figure 3A:
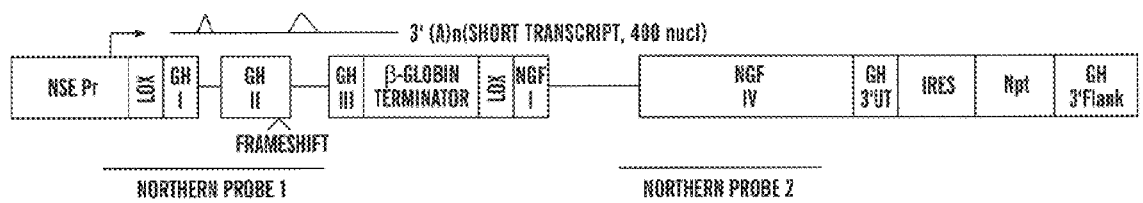
FIG. 3A–B shows northern blot analysis of brain mRNA from NGF-XAT transgenic lines.
Figure 3B:
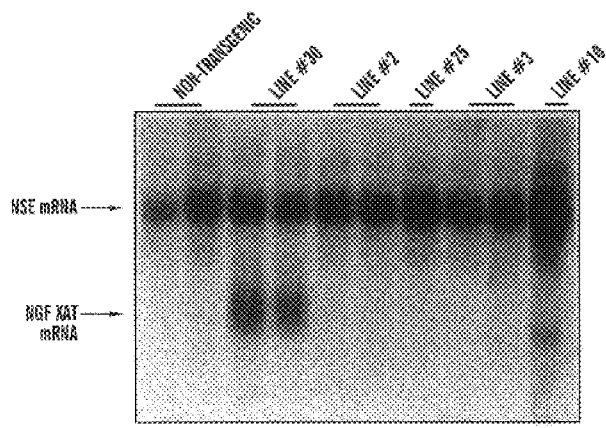
Figure 4A:
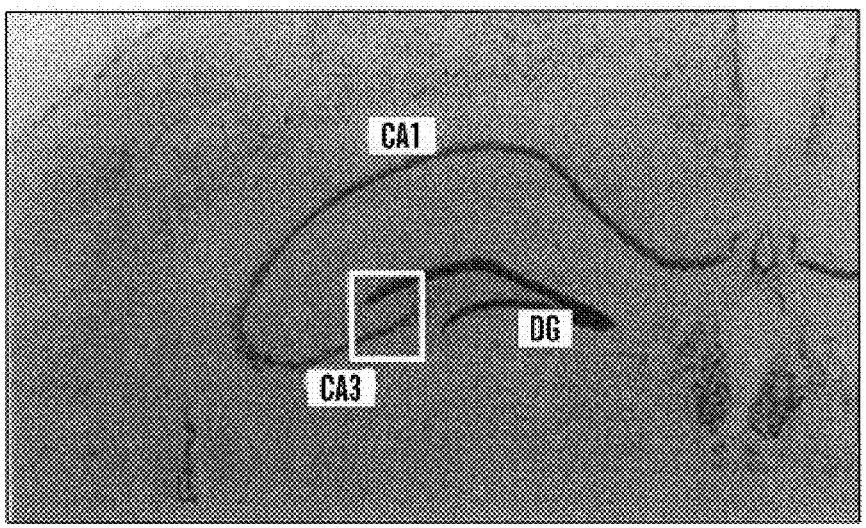
FIG. 4A–C is an in situ hybridization performed on 12 $\mu$m coronal sections using the Digoxigenin labeled oligonucleotide probes (45 mer's) complementary to hGH sequences contained within the NGF-XAT recombinatorial substrate.
Figure 4B:
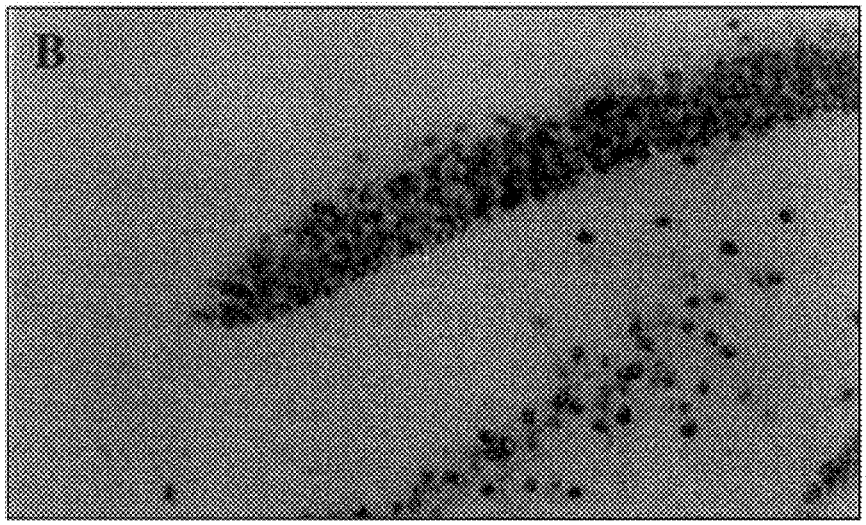
Figure 4C:
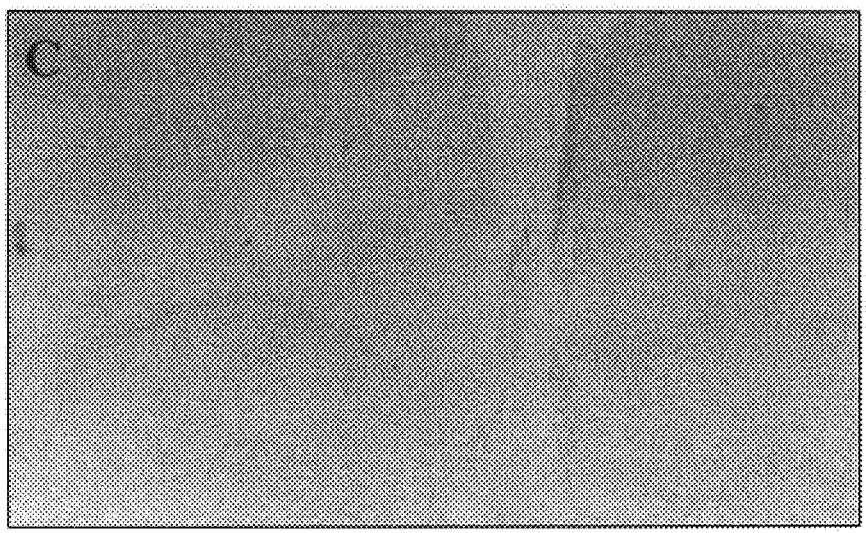

Of the five independent lines of transgenic mice which were generated, two expressed the predicted truncated, inactive transcript (The location of the smaller NGF XAT transcripts in expressing lines #30 and 10 are shown in FIG. 3A). Of the two lines, line #30 produced larger amounts of transcript, that corresponds after correction for the length of probe complementarity to approximately 15% of the amount of the native NSE mRNA (FIG. 3B). In situ hybridization studies using an antisense probe complementary to the truncated, inactive transcript revealed extensive labeling in a neuronal pattern (FIGS. 4A and 4B), whereas transgenic sections probed with a sense probe were negative (FIG. 4C). Additionally, no labeling above background was observed with antisense probe when hybridized to sections from non-transgenic mice. Rehybrization of the blot to Northern Probe 2 (FIG. 4A) revealed no NGF transgene transcripts, confirming efficient transcription termination.

Figure 5A:
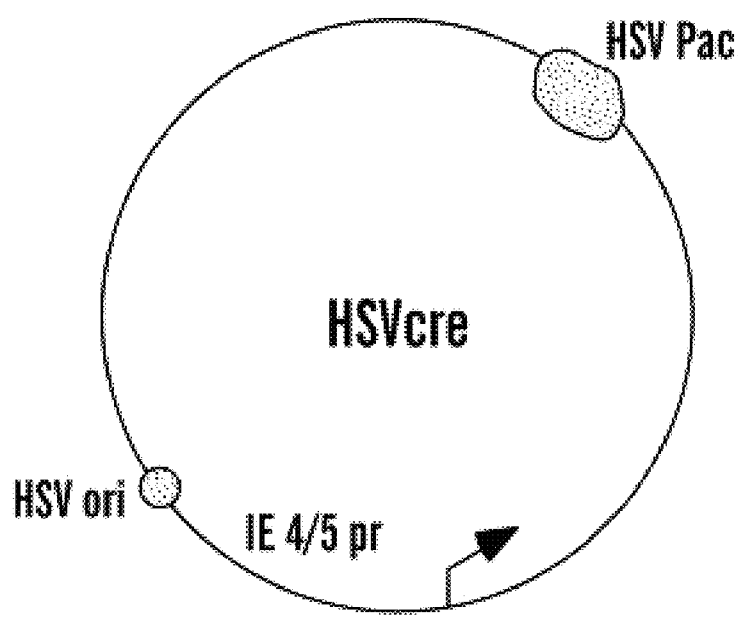
FIG. 5A–E shows HSVcre delivery in vivo to NGF-XAT mice.
Figure 5B:
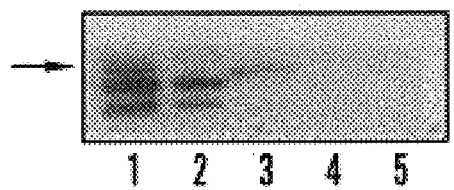
Figure 5C:
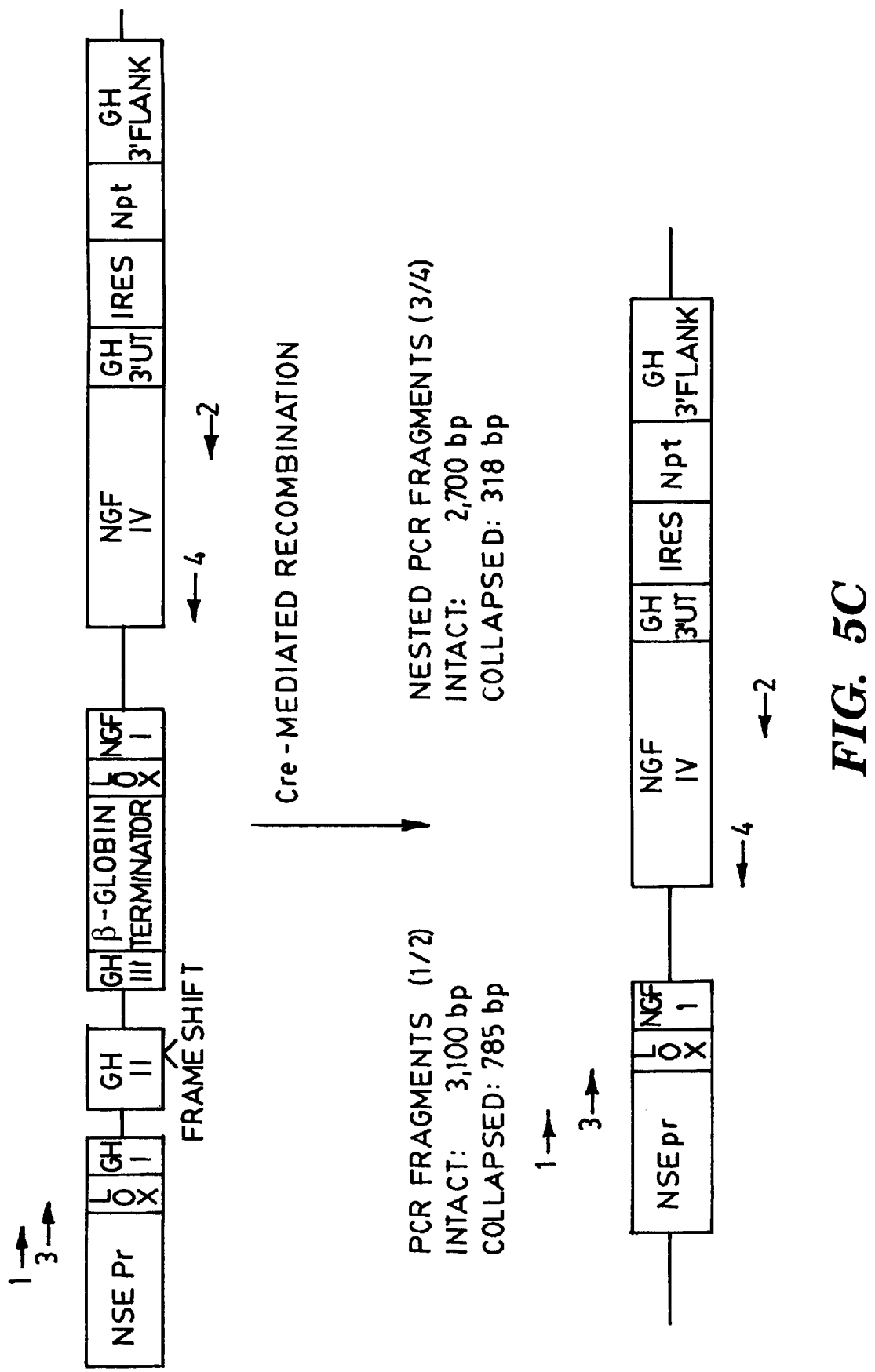

Example 5
Promotion of Recombination in vivo by Somatic Delivery of cre Recombinase To determine whether somatic delivery of cre recombinase could promote recombination in vivo we generated several Herpes Simplex Amplicon (HSV) virus vectors that express recombinase (FIG. 5A; HSVcre). HSVcre was constructed by cloning cre (Gu, H., Zou, Y.-R. and Rajewsky, K., Cell., 73, 1155 (1993)) into HSVPrPUC (Battleman, D., Geller, A. and Chao, M., J Neurosci., 13(3), 941 (1993), Bergold, P., Cassaccia-Bonnefil, P., Xiu-Liu, Z. and Federoff, H., Proc. Natl. Acad. Sci. USA, 90, 6165 (1993), which are hereby incorporated by reference). The gene, HSVcre, was packaged into virus (Geschwind, M., Lu, B. and Federoff, H., Providing pharmacological access to the brain; A volume of Methods in Neurosciences, Conn ed. 1994, which is hereby incorporated by reference) and used to infect NIH3T3 cells to detect recombinase expression. 30 hours later, cells were harvested and protein extracts prepared and subjected to western blot analysis (Hassankhani, A., Steinhelper, M., Soonpaa, M., Katz, E., Taylor, D., Rozenthal, A., Factor, S., Steinberg, J., Field, L. and Federoff, H., Dev Biol., 169, 309 (1995), which is hereby incorporated by reference). Protein extracts from E.coli expressing cre recombinase (FIG. 5B, lane 1) not expressing recombinase (lane 2), HSVcre infected 3T3 cells (lane 3), HSVlac (expresses β-galactosidase) infected 3T3 cells (lane 4), and uninfected 3T3 cells (lane 5) were fractionated by SDS-PAGE, blotted, and probed with a rabbit polyclonal antibody directed against cre recombinase. A cre-specific band (arrow) is observed only in bacteria expressing the recombinase (lane 1) and HSVcre infected 3T3 cells (lane 3). (FIG. 5C) The NGF-XAT construct is depicted before recombination (Top) and after recombination (Bottom) and the location of PCR primers are shown. (FIG. 5D) The PCR was used to monitor Cre recombination in vivo.

Figure 5D:
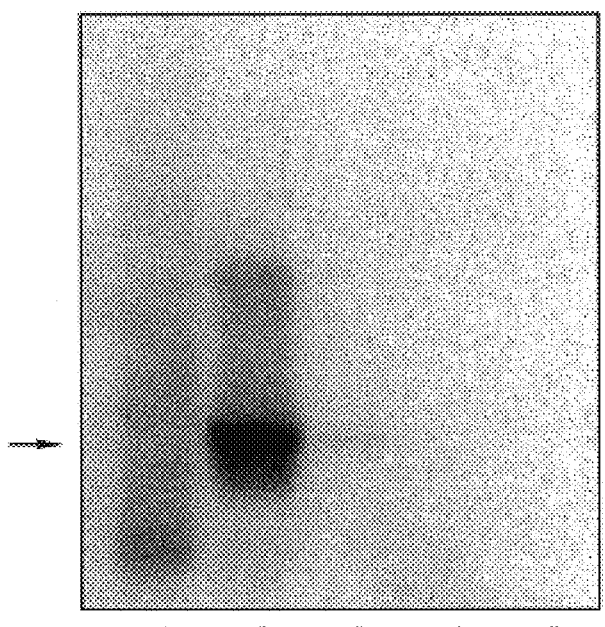
Figure 5E:
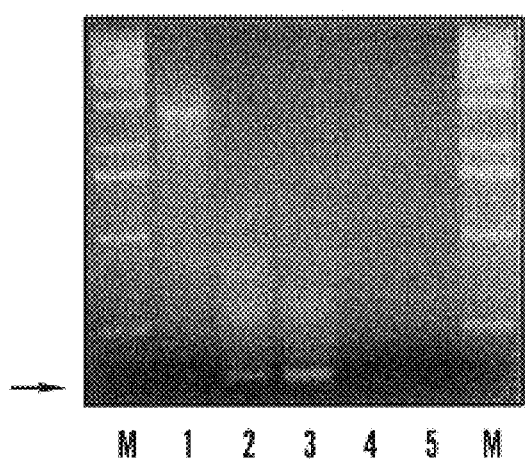

Focal delivery of HSVcre but not control virus HSVlac (expresses β-galactosidase) into the dorsal hippocampus of line #30 mice resulted in excision of the inactivating cassette from the NGF-XAT germline construct (FIG. 5C) as demonstrated as direct PCR-Southern blot analysis (FIG. 5D) and nested PCR (FIG. 5E). Line #30 NGF-XAT mice were infected with HSVcre and HSVlac and brain regions from the injection sites and other noninjected regions harvested. DNA was prepared and subjected to PCR with the primers shown in C (Battleman, D., Geller, A. and Chao, M., J Neurosci., 13(3), 941 (1993), which is hereby incorporated by reference). The PCR products were blotted, hybridized with a $^{32}$P labeled loxP probe, washed stringently and exposed to film as described. A full length 3,100 bp product was observed from a plasmid template containing the non-recombined NGF-XAT (FIG. 5D; lane 1). A collapsed PCR product of 785 bp (arrow) was seen only in brain regions injected with HSVcre virus (FIG. 5D; lane 3) that is the same size as that product derived by PCR on a collapsed template produced by bacteria expressing cre recombinase (FIG. 5D; lane 2). No collapsed PCR fragment was observed in DNA from a HSVlac infected line #30 animal (FIG. 5D; lane 4) or an uninjected animal (FIG. 5D; lane 5). Full length product was not efficiently produced from transgenic line #30 animals, although PCR amplification with HF 37/47 for the NGF minigene (Federoff, H., Geschwind, M., Geller, A. and Kessler, J., Natl. Acad. Sci. USA, 89, 1636 (1992), Hassankhani, A., Steinhelper, M., Soonpaa, M., Katz, E., Taylor, D., Rozental, A., Factor, S., Steinberg, J., Field, L. and Federoff, H., Dev Biol., 169, 309 (1995)) was positive. (FIG 5E) Nested PCR analysis: DNAs extracted from virus infected animals, were amplified with Primers 1/2, reamplified with Primers 3/4, and fractionated on and ethidium bromide agarose gel (Battleman, D., Geller, A. and Chao, M., J Neurosci., 13(3), 941 (1993), which are hereby incorporated by reference). A full length 2,700 bp fragment was observed from a plasmid template containing the non-recombined NGF-XAT (FIG. 5E; lane 1). A collapsed PCR produce of 318 bp (arrow) was observed only in brain regions injected with HSVcre virus (FIG. 5E; lane 3) that is the same size as that product derived by PCR on a collapsed template produced by bacteria expressing cre recombinase (FIG. 5E; lane 2). No collapsed PCR fragment was observed in DNA from a HSVlac-infected line #30 animal (FIG. 5E; lane 4) or an uninjected animal (FIG. 5E; lane 5). Full length product was not efficiently produced from transgenic line #30 animals, although PCR amplification with HF 37/47 for the NGF minigene (Federoff, H., Geschwind, M., Geller, A. and Kessler, J., Natl. Acad. Sci. USA, 89, 1636 (1992), Hassankhani, A., Steinhelper, M., Soonpaa, M., Katz, E., Taylor, D., Rozental, A., Factor, S., Steinberg, J., Field, L. and Federoff, H., Dev Biol., 169, 309 (1995), which are hereby incorporated by reference) was positive.

Example 6
Focal Delivery of cre Expressing HSV Vector

Figure 6A:
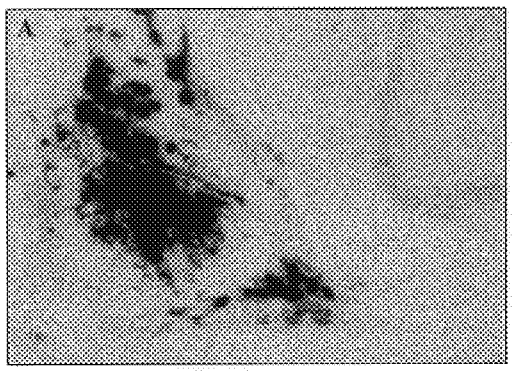
FIGS. 6A–6C are the X-gal histochemistry results to show localization of the vector expression.
Figure 6C:
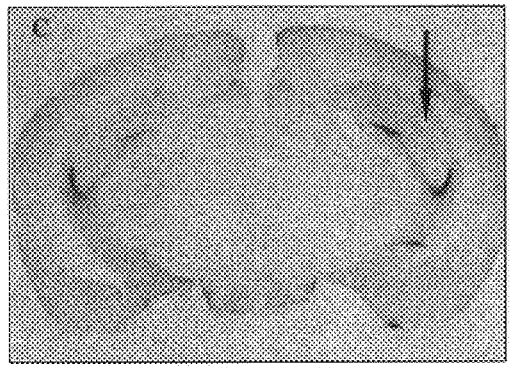
Figure 6B:
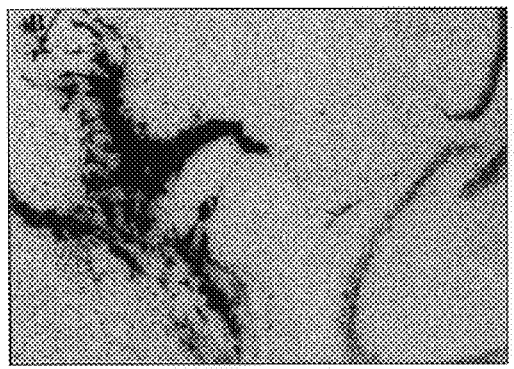
Figure 6D:
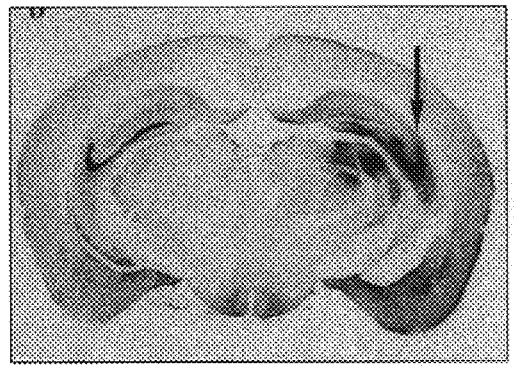
FIG. 6D shows the marked increased in NGF immunoreactivity in the virus injection region.

This example demonstrates that the somatic expression of recombinase activated the NGF-XAT construct for required analysis of the transgene product, NGF, by immunocytochemistry. Line #30 mice were stereotaxically injected unilaterally with either HSVlac or HSVcrelac (expressing both nuclear localized Cre and β-galactosidase) virus (approximately 2×10$^5$ infectious particles). Some animals were analyzed after 4 days to localize expression of β-galactosidase by X-gal histochemistry to confirm localization of vector expression (Geschwind, M., Lu, B. and Federoff, H., Providing pharmacological access to the brain; A volume of Methods in Neurosciences, Conn ed. 1994, which is hereby incorporated by reference). Sections from both HSVlac and HSVcrelac showed robust β-galactosidase expression confined to the virus injection site. A separate group of animals were injected with both viruses and analyzed 14 days later by NGF immunocytochemistry. HSVlac injected animals (FIG. 6C) showed no alteration in the intensity or pattern of immunoreactivity on the injected side (arrow) compared with the control side or uninjected animals (FIGS. 6A, 6B). HSVcrelac infected animals (6D) demonstrated a marked increase in the distribution of NGF immunoreactivity that was localized to the virus injection region (arrow) and not anterior or posterior to the virus injection site (data not shown).

Example 7
Quantification of NGF Immunoreactivity by ELISA

Figure 7:
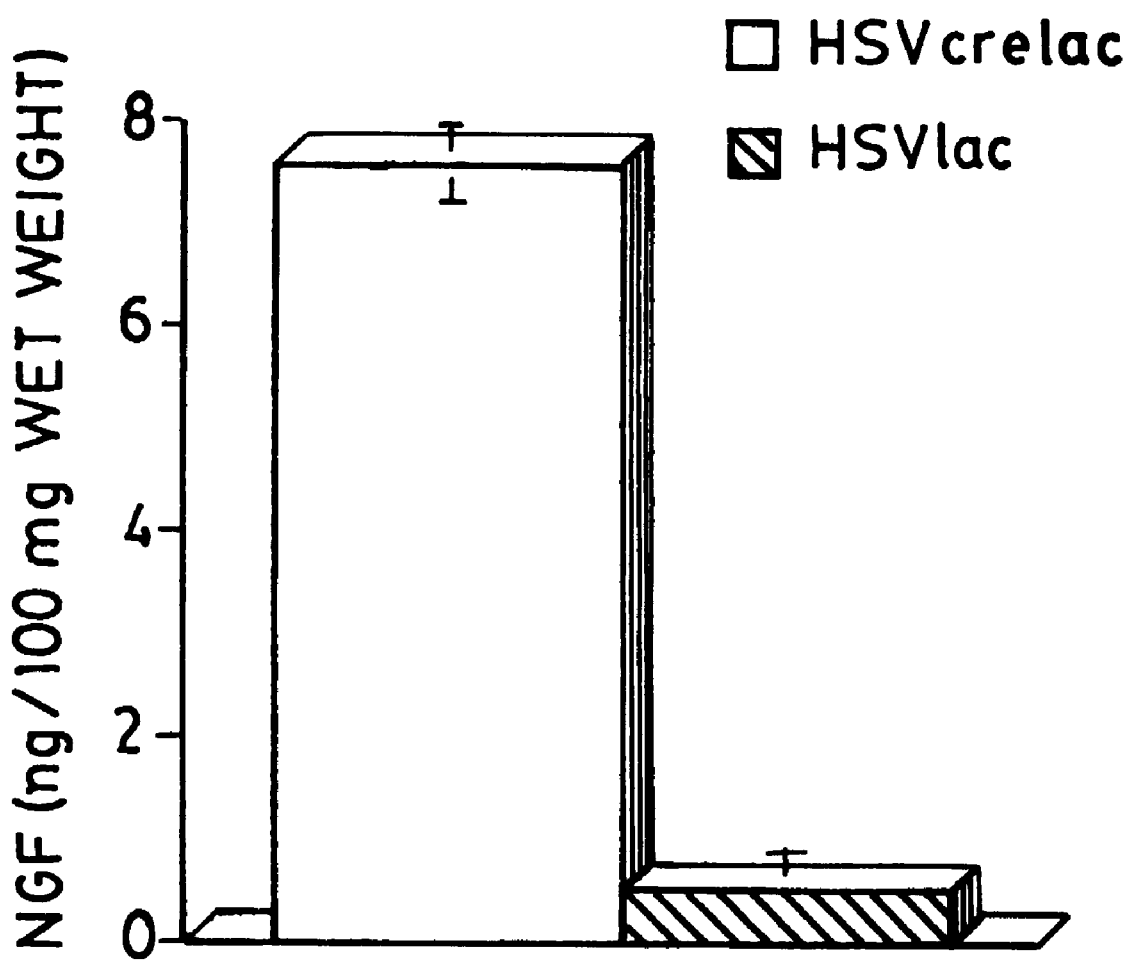
FIG. 7 is a bar graph depicting the NGF content from HSVcrelac and HSVlac injected animals.

Direct quantification of NGF immunoreactivity was performed by ELISA 14 days after virus injection. Line #30 mice were stereotaxically injected unilaterally with either HSVlac or HSVcrelac (expressing both nuclear localized Cre and β-galactosidase) virus (approximately $2\times10^5$ infectious particles), and sacrificed after 14 days. Tissue blocks containing the injection sites were harvested, homogenized, and analyzed by ELISA. A large and significant (*P<0.001, t-test) increase in NGF content was noted in the HSVcrelac (FIG. 7, hatched bar, n=5) compared to the HSVlac (open bar, n=3) injected animals. HSVcrelac injected animals manifest an approximately 15-fold increase in NGF concentration within the injected region as compared to HSVlac and uninjected control animals.

Example 8
Increased Spontaneous Activity in Mice With a cre-activated NGF-XAT Transgene Cre-mediated activation of the NGF-XAT gene within a terminal innervation field of the hippocampus was used to determine whether increased focal NGF function would alter spontaneous behavior. NGF-XAT mice were injected stereotactically into the dorsal hippocampus with either HSVcrelac or control vector HSVlac. Within two weeks, post injection animals injected with HSVcrelac were first noted to be more active. At between 4 and 6 months post injection behavioral studies were performed.

Horizontal and vertical locomotor activity measurements were made in an automated device based on infra-red beam breaks (Octo-Varimex Minor, Columbus Instruments International Corporation) at 5 minute intervals over the course of a 90 minutes experimental session on a single day. Each beam was separated by 25.4 mm. with the width of each beam being 3 mm in diameter. Interruption of any horizontal or vertical beam generated an electrical impulse that was collected using the Octo-M data software. Horizontal beams registered only when the mouse moved in the horizontal plane of the test cage, and jumping and rearing were registered by the vertical beam. Statistical analyses were carried out using 2 way repeated measure analyses of variance with transgene as a between group variable and time interval as a within group variable (SuperANOVA, Abacus Concepts, Inc.).

Line #30 mice were stereotaxically injected unilaterally with either HSVlac or HSVcrelac (expressing both nuclear localized cre and β-galactosidase) virus (approximately $2\times10^5$ infectious particles) and after 4 to 6 months animals were studied behaviorally. The results are summarized in FIG. 8. Total horizontal (top) and vertical (bottom) activity counts during each 5 minute interval over a 90 minutes experimental session for HSVlac (filled circles) and HSVcrelac (open circles) mice. Each data point represents the group mean ±S.E. value and 8 mice for a 5 minutes interval. The groups were age-matched and comprised of 6 males and 2 females.

Horizontal activity levels of HSVcrelac and HSVlac mice were generally equivalent over the first 30 min of the session, but levels subsequently declined less rapidly in HSVcrelac than HSVlac mice over the next 60 min, resulting in significantly higher horizontal activity levels in HSVcrelac mice (main effect of transgene activation, F=8.177, df=1, 14, p=0.012; transgene activation by time interaction, F=2.58, df=17, 238, p=0.0008). Vertical activity levels were likewise significantly increased in HSVcrelac mice (main effect of transgene activation, F=33.29, df=1, 14, p=0.0001) with the increase sustained over the course of the 90 min session (time by transgene activation interaction, F=1.57, df=17, 238, p=0.072). Differences in vertical activity were particularly notable, with peak increases in vertical activity in HSVcrelac mice (time points 7–9) on the order of 1139–1382% of HSVlac values. These increases in activity occurred despite the slightly larger body weights of HSVcrelac mice (HSVcrelac 36.17±S.E. 1.91; HSVlac 31.25 ±S.E. 1.81; p=0.41), which would normally be predicted to decrease motor activity levels. Although the neuroanatomic and physiologic changes underlying this behavioral differences are not yet known, the initiating event is focally increased NGF expression within the hippocampal formation.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

What is claimed:

1. A method of activating a gene to be expressed in a recombinatorial substrate, comprising:

providing a non-human transgenic mammal carrying a DNA molecule comprising a recombinatorial substrate, said recombinatorial substrate comprising:

a promoter element capable of promoting transcription of genes in the recombinatorial substrate;

a gene whose expression is to be controlled, said gene being positioned 3' to the promoter element to facilitate its transcription;

a terminator positioned 3' to said promoter and 5' to said gene whose expression is to be controlled to prevent transcription of genes 3' to said terminator; and a first recombination site located 3' to said terminator and a second recombination site located 5' to said terminator, whereby treatment of said DNA molecule with a recombinase specific to the recombination sites removes said terminator from said DNA molecule, thereby activating the recombinatorial substrate and permitting transcription of said gene whose expression is to be controlled, wherein the transgenic mammal has no gene encoding a recombinase;

introducing into the transgenic mammal, through its somatic cells, a gene encoding a recombinase; and expressing said recombinase, which when expressed in the somatic cells, will promote the excision of DNA from said first recombination site to said second recombination site within the recombinatorial substrate and wherein activation of said gene whose expression is to be controlled confers a detectable and/or functional phenotype on the mammal when expressed in the somatic cells of the mammal.

2. The method of claim 1, wherein said introducing comprises:

providing a vector comprising the gene encoding a recombinase; and introducing the vector directly into the somatic cells of the transgenic mammal.

3. The method of claim 2, wherein the vector is a virus.

4. The method of claim 3, wherein the virus is selected from the group consisting of adenovirus, adeno-associated virus, lentivirus, vaccinia virus, sinbisvirus and retrovirus.

5. The method of claim 1, wherein said introducing is carried out by delivering a nucleic acid molecule comprising the gene encoding a recombinase into the somatic cells of the transgenic mammal by use of virosomes, liposomes, naked DNA, or particle bombardment.

6. The method of claim 1, wherein the recombinase is selected from the group consisting of FLP and cre.

7. The method of claim 1, wherein the mammal is selected from the group consisting of a mouse, rat, goat, cow and pig.

8. A non-human transgenic mammal having a gene activated according to the method of claim 1, wherein the mammal has a genotype characterized by the absence of the gene encoding the recombinase.

9. The transgenic mammal of claim 8, wherein the mammal is selected from the group consisting of a mouse, rat, goat, cow, and pig.

10. A method of activating a recombinatorial substrate, comprising:

providing a non-human transgenic mammal carrying a DNA molecule comprising a recombinatorial substrate, said recombinatorial substrate comprising:

a promoter element capable of promoting transcription of genes in the recombinatorial substrate;

a gene whose expression is to be controlled, said gene being positioned 3' to the promoter element to facilitate its transcription; and a first recombination site located 3' to the gene whose expression is to be controlled and a second recombination site located 5' to the gene whose expression is to be controlled, whereby treatment of said DNA molecule with a recombinase specific to the recombination sites removes said gene whose expression is to be controlled from said DNA molecule, thereby activating the recombinatorial substrate and resulting in a loss of function of said gene whose expression is to be controlled, wherein the transgenic mammal has no gene encoding a recombinase;

introducing into the transgenic mammal, through its somatic cells, a gene encoding a recombinase;

expressing said recombinase, which when expressed in the somatic cells, will promote the excision of DNA from said first recombination site to said second recombination site within the recombinatorial substrate and wherein activation of said recombinatorial substrate confers a detectable and/or functional phenotype on the mammal.

11. The method of claim 10, wherein said introducing comprises:

providing a vector comprising the gene encoding a recombinase; and introducing the vector directly into the somatic cells of the transgenic mammal.

12. The method of claim 11, wherein the vector is a virus.

13. The method of claim 12, wherein the virus is selected from the group consisting of adenovirus, adeno-associated virus, lentivirus, vaccinia virus, sinbisvirus, and retrovirus.

14. The method of claim 10, wherein said introducing is carried out by delivering a nucleic acid molecule comprising the gene encoding a recombinase into the somatic cells of the transgenic mammal by use of virosomes, liposomes, naked DNA, or particle bombardment.

15. The method of claim 10, wherein the recombinase is selected from the group consisting of FLP and cre.

16. The method of claim 10, wherein the mammal is selected from the group consisting of a mouse, rat, goat, cow and pig.

17. A non-human transgenic mammal having a recombinatorial substrate activated according to the method of claim 10, wherein the mammal has a genotype characterized by the absence of the gene encoding the recombinase.

18. The transgenic mammal of claim 17, wherein the mammal is selected from the group consisting of a mouse, rat, goat, cow, and pig.

* * * * *